United States Patent
Christopher et al.

(10) Patent No.: US 10,584,111 B2
(45) Date of Patent: *Mar. 10, 2020

(54) 4-(3-CYANOPHENYL)-6-PYRIDINYLPYRIMIDINE MGLU5 MODULATORS

(71) Applicant: Heptares Therapeutics Limited, Cambridge (GB)

(72) Inventors: John Andrew Christopher, Cambridge (GB); Miles Stuart Congreve, Cambridge (GB); Sarah Joanne Aves, Cambridge (GB); Benjamin Gerald Tehan, Cambridge (GB)

(73) Assignee: Heptares Therapeutics Limited, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/280,512

(22) Filed: Feb. 20, 2019

(65) Prior Publication Data

US 2019/0177297 A1    Jun. 13, 2019

Related U.S. Application Data

(63) Continuation of application No. 15/618,504, filed on Jun. 9, 2017, now Pat. No. 10,246,432, which is a continuation of application No. 14/904,907, filed as application No. PCT/GB2014/052184 on Jul. 17, 2014, now Pat. No. 9,676,745.

(30) Foreign Application Priority Data

Jul. 17, 2013   (GB) .................................... 1312800.4

(51) Int. Cl.
C07D 401/04    (2006.01)
C07D 403/04    (2006.01)
C07D 239/26    (2006.01)

(52) U.S. Cl.
CPC ......... *C07D 401/04* (2013.01); *C07D 239/26* (2013.01); *C07D 403/04* (2013.01)

(58) Field of Classification Search
CPC ... C07D 401/04; C07D 239/26; C07D 403/04
See application file for complete search history.

(56) References Cited

U.S. PATENT DOCUMENTS

| | | | |
|---|---|---|---|
| 9,676,715 B2 | 6/2017 | Denis et al. | |
| 9,676,745 B2 * | 6/2017 | Christopher | C07D 401/04 |
| 10,246,432 B2 * | 4/2019 | Christopher | C07D 401/04 |
| 2005/0020585 A1 | 1/2005 | Cosford et al. | |
| 2007/0105871 A1 | 5/2007 | Schiemann et al. | |

FOREIGN PATENT DOCUMENTS

| | | |
|---|---|---|
| WO | 2003/051315 A2 | 6/2003 |
| WO | 2004/084824 A2 | 10/2004 |
| WO | 2005/066155 A1 | 7/2005 |
| WO | 2005/080397 A2 | 9/2005 |
| WO | 2009/011850 A2 | 1/2009 |
| WO | 2010/017179 A1 | 2/2010 |
| WO | 2011/091153 A1 | 7/2011 |
| WO | 2012/003912 A1 | 1/2012 |

OTHER PUBLICATIONS

Kavirajan et al., Efficacy and adverse effects of cholinesterase inhibitors and memantine in vascular dementia: a meta-analysis of randomised controlled trials. Lancet Neurol. Sep. 2007;6(9):782-92.
STN Registry No. 959547-01-4, Benzonitrile, 3-[6-(1H-imidazol-1-yl)-4-pyrimidinyl]. 1 page, Dec. 26, 2007.
Vattakatuchery et al., Acetylcholinesterase inhibitors in cognitive impairment in Huntington's disease: A brief review. World J Psychiatry. Sep. 22, 2013;3(3):62-4.
Wang et al., Role of Glutamate and NMDA Receptors in Alzheimer's Disease. J Alzheimers Dis. 2017;57(4):1041-1048.
International Search Report and Written Opinion for Application No. PCT/GB2014/052184, dated Sep. 18, 2014.
United Kingdom Search Report for Application No. GB1312800.4, dated Dec. 13, 2013.

* cited by examiner

*Primary Examiner* — Pancham Bakshi
(74) *Attorney, Agent, or Firm* — McCarter & English, LLP; Steven G. Davis; Mei Bai

(57) ABSTRACT

The disclosures herein relate to novel compounds of formula wherein $R_1$, $R_2$, $R_3$ and $R_4$ and n are defined herein, and their use in treating, preventing, ameliorating, controlling or reducing the risk of inflammation, neurological or psychiatric disorders associated with modulating mGlu5 receptor function.

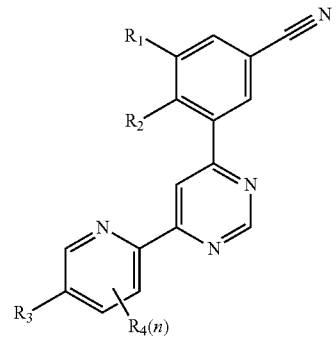

15 Claims, 1 Drawing Sheet

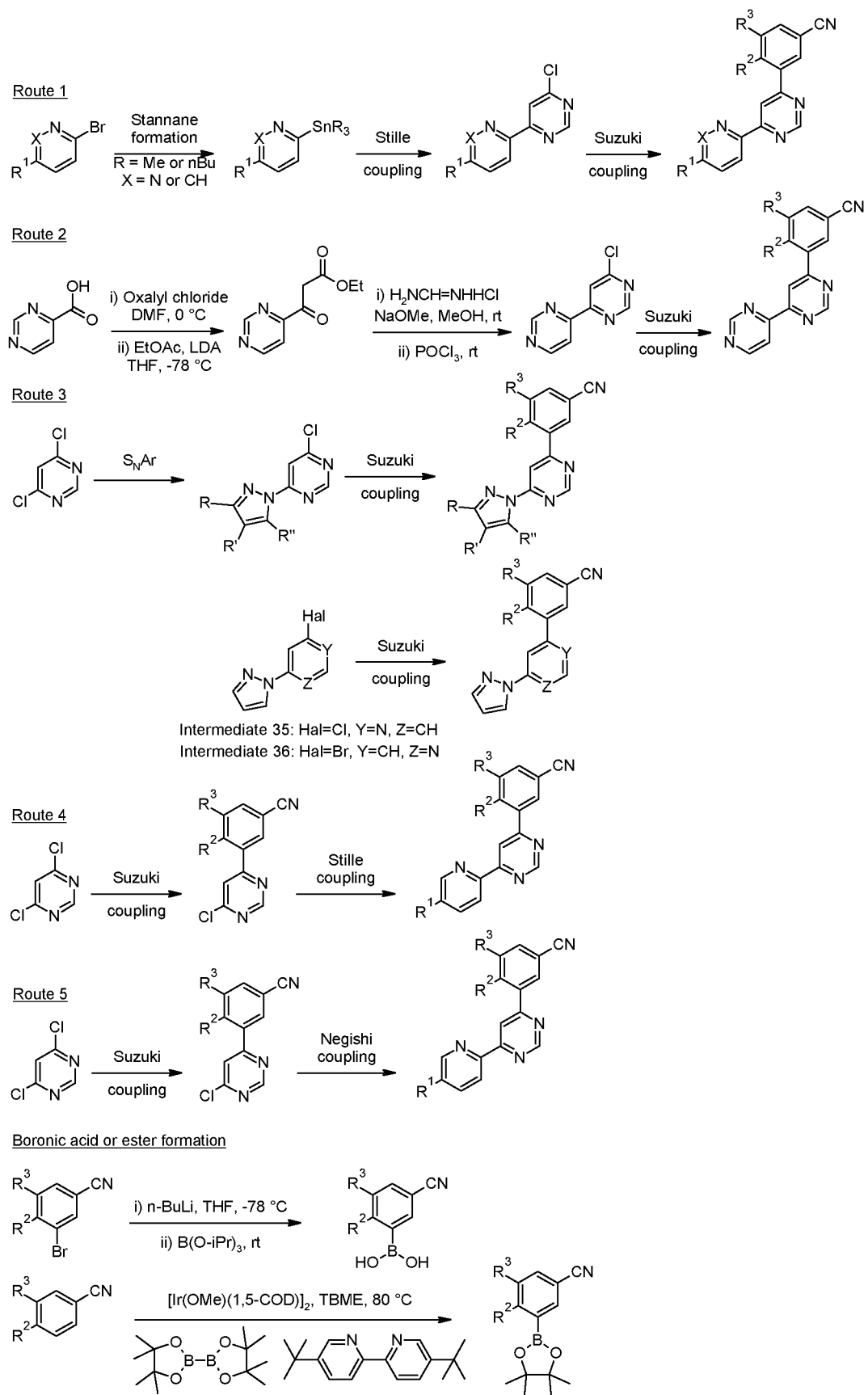

ically located post-synaptically and couple through the $G_{q/11}$ pathway. Group II is comprised of mGlu2 and mGlu3 receptors and group III of mGlu4, mGlu6, mGlu7 and mGlu8 receptors; both group II and group III receptors are located pre-synaptically and primarily couple through $G_{i/o}$.

4-(3-CYANOPHENYL)-6-PYRIDINYLPYRIMIDINE MGLU5 MODULATORS

RELATED APPLICATION INFORMATION

This application is a continuation of U.S. patent application Ser. No. 15/618,504, filed Jun. 9, 2017, which is a continuation of U.S. patent application Ser. No. 14/904,907, filed Jan. 13, 2016, now U.S. Pat. No. 9,676,745, which is a 371 of International Patent Application PCT/GB2014/052184, filed Jul. 17, 2014, which claims priority to GB Application No.: 1312800.4, filed Jul. 17, 2013. The entire contents of these applications are incorporated herein by reference in their entirety.

This application relates to novel compounds and their use as mGlu5 modulators. Compounds described herein may be useful in the treatment or prevention of diseases in which glutamatergic neurotransmission is involved. The application is also directed to pharmaceutical compositions comprising these compounds and the manufacture and use of these compounds and compositions in the prevention or treatment of such neuropathological diseases.

BACKGROUND OF THE INVENTION

Glutamate is the major excitatory neurotransmitter in the brain. Glutamate exerts its actions through both ionotropic and metabotropic glutamate receptors. There are eight metabotropic glutamate (mGlu) receptors belonging to the class C G protein-coupled receptor (GPCR) family. The eight mGlu receptors can be further divided into three groups based on their sequence similarity, pharmacological profiles and transduction mechanisms. The mGlu1 and mGlu5 receptors belong to group I; these receptors are primarily located post-synaptically and couple through the $G_{q/11}$ pathway. Group II is comprised of mGlu2 and mGlu3 receptors and group III of mGlu4, mGlu6, mGlu7 and mGlu8 receptors; both group II and group III receptors are located pre-synaptically and primarily couple through $G_{i/o}$. The mGlu receptors are composed of three distinct regions; the extracellular (Venus fly-trap domain), transmembrane and intracellular regions. Glutamate binds to the extracellular site. Modulators bind to the transmembrane domains where they can act to enhance (positive allosteric modulators or PAMs) or decrease (negative allosteric modulators or NAMs) the activity of glutamate. The mGlu receptors are involved in the fine tuning of neuronal responses and changes in glutamatergic signalling have been implicated in a wide range of disease processes in humans and other species (e.g. see Yasuhara and Chaki, The Open Medicinal Chemistry Journal, 2010, 4, 20-36). Thus modulating the activity of glutamatergic signalling may be efficacious in the treatment of a variety of neurological and psychiatric disorders.

The present invention relates to modulators of metabotropic glutamate receptors, in particular the mGlu5 receptor. The mGlu5 receptor is abundant throughout the cortex, hippocampus, striatum, caudate nucleus and nucleus accumbens, areas involved in emotion, motivational processes and cognitive function. Compounds that act at the mGlu5 receptor have utility in treating, preventing, ameliorating, controlling or reducing the risk of multiple conditions; those of particular importance include one or more of the following: dementia (including senile dementia and dementia caused by AIDS), pain (including headaches (such as migraine and cluster headaches), inflammatory pain (such as inflammatory tongue pain), visceral pain syndromes (such as painful bladder syndrome), gastro-intestinal pain (including irritable bowel syndrome), itch, fibromyalgia, disorders of the urinary tract (including incontinence, prostatitis, urinary frequency, nocturia, overactive bladder, cystitis, benign prostatic hyperplasia, detrusor hyperreflexia, outlet obstruction, urinary urgency, pelvic hypersensitivity, urge incontinence, urethritis, prostatodynia, idiopathic bladder hypersensitivity), substance-related disorders (including addiction, alcohol abuse, alcohol dependence, alcohol withdrawal, amphetamine dependence, amphetamine withdrawal, cocaine dependence, cocaine withdrawal, opioid dependence, opioid withdrawal), anxiety disorders (including agoraphobia, generalized anxiety disorder (GAD), obsessive compulsive disorder (OCD), panic disorder, post-traumatic stress disorders, social and specific phobias, substance-induced anxiety disorder), eating disorders (including obesity, anorexia and bulimia), attention-deficit/hyperactivity disorder (ADHD; ADD), deficits and abnormalties in attention and vigilance, executive functions and memory, movement disorders (including Parkinson's disease, levodopa-induced dyskinesias, Tourette's syndrome, Huntington's disease, dystonias, restless leg syndrome, simple tics, complex tics and symptomatic tics, periodic limb movement syndromes), amyotrophic lateral sclerosis (ALS), multiple sclerosis, schizophrenia, cancer (including melanoma, squamous cell carcinoma and astrocytoma), mood disorders (including major depressive disorder, dysthymia, treatment-resistant depression and bipolar disorders I and II), rare neurological diseases including inherited diseases and developmental disorders (including autistic spectrum disorders [Asperger's syndrome, Rett's syndrome, Pervasive Development Disorder Not Otherwise Specified, Childhood Disintegrative Disorder] and Down's syndrome), fragile X syndrome and other areas of mental retardation, disorders of the gastro-intestinal tract (including gastroesophageal reflux disease, functional dyspepsia, functional heartburn, irritable bowel syndrome, functional bloating, functional diarrhoea, chronic constipation, post-operative ileus), epilepsy, retinopathy, neuroprotection (including Alzheimer's disease, stroke, status epilepticus and head injury), ischemias (including cerebral ischameia especially acute ischemia, ischemic diseases of the eye), muscle spasms (such as local or general spasticity), autoimmune disorders of the nervous system including paraneoplastic syndromes, spinal muscular atrophy, vomiting, skin disorders and any other disorders associated with irregularities of glutamatergic signal transmission.

It has been suggested that the glutamatergic system is a mediator of psychiatric pathology and that, potentially, it is a common pathway for therapeutic action of antidepressant medications (Sanacora et al., Neuropharmacology, 2012, 62, 63-77). The mGlu5 receptor is located on GABAergic interneurones in the hippocampus and prefrontal cortex; inhibition of mGlu5 on these neurones may lead to the disinhibition of intermediate interneurones, ultimately resulting in a decrease in glutamatergic transmission (Chaki et al., Neuropharmacology, 2012, 66, 40-52). It has been shown that acute administration of an mGlu5 NAM (GRN-529) is efficacious in reducing depression (decreasing mobility time in tail suspension test and forced swim test), anxiety (by attenuation of stress-induced hyperthermia) and pain (reversal of hyperalgesia due to sciatic nerve ligation) (Hughes et al., Neuropharmacology, 2012, 66, 202-214). mGlu5 modulators may therefore be useful in the treatment of depression, anxiety and other mood disorders and pain.

Activity of mGlu5 antagonists/NAMs as analgesics has been demonstrated in models of inflammatory pain. In the Complete Freund's adjuvant-injected tongue (a model of inflammatory tongue pain) a selective mGlu5 antagonist significantly depressed mechanical allodynia and heat hyperalgesia whilst continuous intrathecal administration of a selective mGlu5 agonist induced allodynia in naive rats (Liu et al., Journal of Neuroinflammation, 2012, 9:258). NAMs and antagonists of the mGlu5 receptor may have efficacy in reducing visceral pain syndromes. For example, in painful bladder syndrome (a type of visceral pain syndrome) the pharmacological activation of mGlu5 receptors in the central nucleus of the amygdala (a critical site for neuromodulation for processing of bladder nociception) has been shown to lead to increase the response to bladder distension that drives bladder pain sensitization (Crock et al., Journal of Neuroscience, 2012, 32, 14217-14226). Glutamate receptors are distributed in pain relay structures with glutamate having a key role in trigerninovascular activation, central sensitization and cortical spreading depression (CSD); areas that are important for migraine and cluster headache pathophysiology (Monteith & Goadsby, Current Treatment Options in Neurology, 2011, 13, 1-14). A specific role of mGlu5 in central sensitisation was demonstrated by the induction of long-term potentiation in the superficial layer of the trigeminal nucleus caudalis by electrical stimulation of the mandibular nerve by the mGlu5 agonist CHPG which was selectively blocked by the mGlu5 NAM MPEP (Liang et al, Pain, 2005, 114, 417-428).

The mGlu5 receptor plays a critical role in behavioural responses to multiple substances of abuse and may therefore have a role in the treatment of substance abuse related disorders. The mGlu5 receptor is located in brain regions thought to participate in reward-related behaviours such as the bed nucleus of the stria terminalis. Acute pharmacological antagonism of the mGlu5 receptor has been shown to disrupt the reinforcing properties of, for example, pyschostimulants (e.g. cocaine; Grueter et al., The Journal of Neuroscience, 2008; 28, 9261-9270), alcohol (Blednov and Harris, The International Journal of Neuropsychopharmacology 2008, 11, 775-793) and nicotine (Palmatier et al., Neuropsychopharmacology 2008, 33, 2139-2147).

Benzodiazepines are generally regarded as effective anxiolytics but suffer from dose-limiting side effects including sedation, memory impairment and abuse whilst selective-serotonin re-uptake inhibitors suffer from long onset of action. The mGlu5 receptor is expressed in several brain regions associated with anxiety and may play a role in treatment of anxiety disorders. The mGlu5 NAM fenobam was demonstrated to have anxiolytic effects in multiple animal models (stress-induced hyperthermia model, Vogel conflict test, Geller-Seifter conflict test, conditioned emotional response test) (Porter et al., The Journal of Pharmacology and Experimental Therapeutics, 2005, 315, 711-721). The mGlu5 NAM fenobam also showed efficacy in phase II trials of generalized anxiety disorder (GAD).

Proton spectroscopy has shown an increase in glutamatergic resonance in the right prefrontal cortex and left striatum in attention deficit hyperactivity disorder (ADHD) children compared to healthy controls, with the resonance in the prefrontal cortex correlating with age of onset of ADHD symptoms (MacMaster et al, Biological Psychiatry, 2003, 53, 184-187). Copy number variant association analysis in patients with ADHD have shown variations in the gene encoding the mGlu5 receptor (GRM5) and other glutamatergic signalling pathway genes (Elia et al., Molecular Psychiatry, 2010, 15, 637-646). This suggests that alteration in glutamatergic signalling via mGlu5 antagonism or negative allosteric modulation may be a treatment strategy for ADHD/ADD.

The substantia nigra is a key nucleus in the basal ganglia motor circuit playing a key role in motor function. The mGlu5 receptor is involved in direct excitation of substantia nigra neurones which increase firing frequency and burst-firing activity (Awad et al., Journal of Neuroscience, 2001, 20, 7891-7879). The substantia nigra is the primary site of pathology in a number of movement disorders including Parkinson's disease (PD), Tourette's and Huntington's disease. PD is characterised by the loss of dopamine producing neurones in the substantia nigra. Current treatments for PD include levodopa therapy to counteract the loss of dopamine, although this treatment leads to the development of levodopa-induced dyskinesias (LID). There are two types of dyskinesia, chorea (rapid uncontrolled movements) and dystonia (slow writhing movements). The loss of dopaminergic neurones in the striatum causes an increase in the glutamatergic output from the substantia nigra. Antagonism of the mGlu5 receptor is clinically validated in reducing PD-LID, showing a clinically relevant and significant anti-dyskinetic effect without changing anti-parkisonian effects of dopaminergic therapy and may be useful in the treatment of other movement disorders. Antagonists or negative allosteric modulators of mGlu5 also have the potential to treat anxiety and depression which are high co-morbidities in PD. Studies with the mGlu5 NAM dipraglurant shows efficacy in reversing both chorea and dystonias and dipraglurant is reported to be entering clinical trials as a treatment for other rare dystonias.

In Huntington's disease and Tourette's syndrome there is a decrease in activity in the substantia nigra hence agonists and PAMs of mGlu5 are of interest as therapeutic treatments in these disease settings. In a mouse model of Huntington's disease mGlu5 PAMs were shown to be neuroprotective, protecting striatal neurones from excitotoxic cell death (Doria et al., British Journal of Pharmacology, 2013, 169, 909-921). Positive allosteric modulators of the mGlu5 receptor may be useful in treatment of positive and negative symptoms of schizophrenia, and have been shown to have anti-psychotic effects in rat behavioural models (Kinney et al., The Journal of Pharmacology and Experimental Therapeutics, 2005, 313, 199-206). The mGlu5 receptor synergistically facilitates NMDA receptor function and mGlu5 PAMs are in pre-clinical trials for the treatment of schizophrenia.

The mGlu5 receptor has been implicated in the growth and migration of many types of non-neuronal cancers including squamous cell carcinoma (Park et al., Oncology reports, 2007, 17, 81-87) and melanoma (Choi et al., PNAS, 2011, 108, 15219-15224) and therefore modulators of mGlu5 may play a role in the treatment of cancer.

Fragile X syndrome (FXS) is a monogenic disease that causes reduction in the levels of fragile X mental retardation peptide 1 (Fmrp1). Fmrp1 works in functional opposition to mGlu5; reduction in Fmrp1 leads to increased mGlu5 signalling. There is good pre-clinical evidence that FXS can be modified by pharmacological intervention; in mouse models (Fmr1 knock-out) symptoms and neuropathology of FXS can be rescued by mGlu5 antagonism (Michalon et al., Neuron, 2012, 74, 49-56) and the mGlu5 negative allosteric modulator (NAM) mavoglurant has been evaluated in phase III clinical trials for the treatment of FXS. FXS is the highest known risk factor for developing autistic spectrum disorders. Under the DSM-IV classification autistic spectrum disorders (ASDs) include autism, Asperger's syndrome, Pervasive Developmental Disorder-Not Otherwise Specified, Rett's syndrome and childhood Disintegrative Disorder. ASDs are characterised by impairments in social interaction, communication and language development and the presence of restricted interests or repetitive behaviours. Hyperactivity in glutamatergic signalling has been implicated in ASDs suggesting mGlu5 antagonism may be therapeutically beneficial for treatment of ASDs.

The most common neurological abnormality in FXS is epilepsy. There is long lasting functional enhancement of group I mGlu receptors in models of epilepsy such as the amygdala-kindled rat (Tang et al., Current Neuropharmacology, 2005, 3, 299-307). mGlu5 receptor negative allosteric modulators have been shown to block seizures in mouse models of epilepsy (Chapman et al., Neuropharmacology, 2000, 39, 1567-1574).

Gastroesophogeal reflux disease (GERD) is frequently caused by transient lower esophageal sphincter relaxation (TLESR), a mechanism thought to be partly regulated by the mGlu5 receptor. A proof-of-concept trial showed a negative allosteric modulator of mGlu5 (ADX10059) had efficacy in the treatment of GERD by significantly decreasing the time with pH<4 throughout a 24 h period and reducing the number and duration of symptomatic reflux episodes (Keywood et al., Gut, 2009, 58, 1192-1199).

Selective blockade of the mGlu5 receptor potently protects cultured cortical neurones against NMDA or β-amyloid toxicity and also against neurodegeneration in in vivo models (Bruno et al., Neuropharmacology 2000, 39, 2223-2230). It is widely accepted that amyloid β contributes to the pathogenesis of Alzheimer's disease. The mGlu5 receptor has been shown to be a co-receptor for amyloid β oligomers bound to cellular prion protein to activate the intracellular Fyn kinase (Um et al., Neuron, 2013, 79, 887-902). Activation of the mGlu5 receptor removes the repressive effect of fragile X mental retardation peptide 1 on amyloid precursor protein mRNA translation (a precursor to amyloid β) (Sokol et al., Neurology, 2011, 76, 1344-1352). The amyloid β-mediated impairment of long term potentiation can be attenuated by co-treatment with mGlu5 NAM MPEP (Wang et al., The Journal of Neuroscience, 2004, 24, 3370-3378), suggesting that mGlu5 negative allosteric modulators may play a role in neuroprotection.

Amyotrophic lateral sclerosis (ALS; also known as motor neurone disease) is a neurological disorder characterised by motor neurone degeneration. Mutations in the superoxide dismutase 1 (SOD1) enzyme have been linked to familial amyotrophic lateral sclerosis. The mGlu5 NAM MPEP has shown efficacy in a mouse model of ALS (hSOD1$^{G93A}$) with MPEP delaying disease onset, increasing survival and slowing astrocytic degeneration (Rossi et al., Cell Death Differ. 2008, 15, 1691-1800). An up-regulation of mGlu5 expression is seen in ALS spinal cord compared to control (Aronica et al., Neuroscience, 2001, 105, 509-520).

SUMMARY OF THE INVENTION

Disclosed herein are novel compounds, and the first medical use of said compounds. The invention also relates to the first medical use of both novel and known compounds as negative allosteric modulators of mGlu5.

Compounds of the invention include compounds of formula (1)

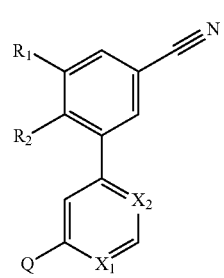

(1)

where $R_1$ is halogen, optionally substituted $C_1$-$C_3$ alkyl, cyclopropyl, optionally substituted $C_1$-$C_3$ alkoxy, cyano, hydroxyl, nitro or $NH_2$;

$R_2$ is H or F;

$X_1$ and $X_2$ are CH or N, where one or both $X_1$ or $X_2$ is N; and

Q is an optionally substituted 5 or 6 membered monocyclic aromatic heterocyclic group.

Q may be an optionally substituted pyrazyl, pyridyl, oxazyl, thiazyl or diazinyl.

Compounds may include compounds of formula 2

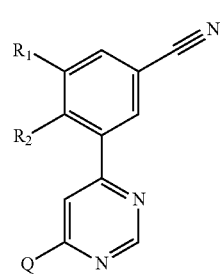

(2)

where $R_1$ is halogen, optionally substituted $C_1$-$C_3$ alkyl, cyclopropyl, optionally substituted $C_1$-$C_3$ alkoxy, cyano, hydroxyl, nitro or $NH_2$;

$R_2$ is H or F; and

Q is an optionally substituted pyridyl or pyrazyl group.

Compounds may include compounds of formula 3

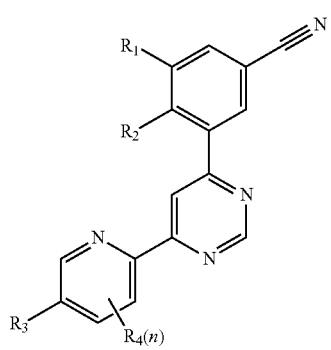

(3)

where $R_1$ is halogen, optionally substituted $C_1$-$C_3$ alkyl, cyclopropyl, optionally substituted $C_1$-$C_3$ alkoxy, cyano, hydroxyl, nitro or $NH_2$;

R$_2$ is H or F;

R$_3$ is H, halogen, optionally substituted C$_1$-C$_3$ alkyl, optionally substituted C$_1$-C$_3$ alkoxy, cyano or a ring N;

R$_4$ is H, halogen, optionally substituted C$_1$-C$_3$ alkyl, optionally substituted C$_1$-C$_3$ alkoxy, cyano or a ring N and n is 0-3.

Compounds may include compounds of formula 4

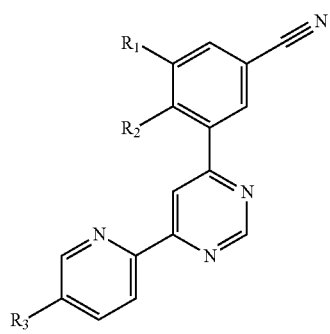

(4)

where R$_1$ is halogen, optionally substituted C$_1$-C$_3$ alkyl, cyclopropyl, optionally substituted C$_1$-C$_3$ alkoxy, cyano, hydroxyl, nitro or NH$_2$;

R$_2$ is H or F; and

R$_3$ is H, halogen, optionally substituted C$_1$-C$_3$ alkyl, optionally substituted C$_1$-C$_3$ alkoxy, cyano or a ring N;

Compounds may include compounds of formula 5

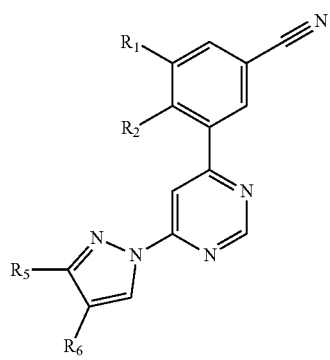

(5)

where R$_1$ is halogen, optionally substituted C$_1$-C$_3$ alkyl, cyclopropyl, optionally substituted C$_1$-C$_3$ alkoxy, cyano, hydroxyl, nitro or NH$_2$;

R$_2$ is H or F;

R$_5$ is H, D, halogen, optionally substituted C$_1$-C$_3$ alkyl or cyano; and

R$_6$ is H, D, halogen, optionally substituted C$_1$-C$_3$ alkyl or cyano.

FIGURES

FIG. 1 shows a variety of synthetic routes to compounds of the invention.

DETAILED DESCRIPTION OF THE INVENTION

The invention relates to novel compounds. In the cases where compounds are novel, the compounds themselves may be claimed. In cases where the compounds have been synthesised previously, but no medical use has been reported, the first medical use of known compounds may be claimed. The invention also relates to the use of both novel and known compounds as antagonists or negative allosteric modulators of mGlu5. The invention further relates to the use of compounds in the manufacture of medicaments for use as mGlu5 receptor antagonists or negative allosteric modulators. The invention further relates to compounds, compositions and medicaments for the treatment of dementia (including senile dementia and dementia caused by AIDS), pain (including headaches (such as migraine and cluster headaches), inflammatory pain (such as inflammatory tongue pain), visceral pain syndromes (such as painful bladder syndrome), gastro-intestinal pain (including irritable bowel syndrome), itch, fibromyalgia), disorders of the urinary tract (including incontinence, prostatitis, urinary frequency, nocturia, overactive bladder, cystitis, benign prostatic hyperplasia, detrusor hyperreflexia, outlet obstruction, urinary urgency, pelvic hypersensitivity, urge incontinence, urethritis, prostatodynia, idiopathic bladder hypersensitivity), substance-related disorders (including addiction, alcohol abuse, alcohol dependence, alcohol withdrawal, amphetamine dependence, amphetamine withdrawal, cocaine dependence, cocaine withdrawal, opioid dependence, opioid withdrawal), anxiety disorders (including agoraphobia, generalized anxiety disorder (GAD), obsessive compulsive disorder (OCD), panic disorder, post-traumatic stress disorders, social and specific phobias, substance-induced anxiety disorder), eating disorders (including obesity, anorexia and bulimia), attention-deficit/hyperactivity disorder (ADHD; ADD), deficits and abnormalties in attention and vigilance, executive functions and memory, movement disorders (including Parkinson's disease, levodopa-induced dyskinesias, Tourette's syndrome, Huntington's disease, dystonias, restless leg syndrome, simple tics, complex tics and symptomatic tics, periodic limb movement syndromes), aniyotrophic lateral sclerosis (ALS), multiple sclerosis, schizophrenia, cancer (including melanoma, squamous cell carcinoma and astrocytoma), mood disorders (including major depressive disorder, dysthymia, treatment-resistant depression and bipolar disorders I and II), rare neurological diseases including inherited diseases and developmental disorders (including autistic spectrum disorders [Asperger's syndrome, Rett's syndrome, Pervasive Development Disorder Not Otherwise Specified, Childhood Disintegrative Disorder] and Down's syndrome), fragile X syndrome and other areas of mental retardation, disorders of the gastro-intestinal tract (including gastroesophageal reflux disease, functional dyspepsia, functional heartburn, irritable bowel syndrome, functional bloating, functional diarrhoea, chronic constipation, post-operative ileus), epilepsy, retinopathy, neuroprotection (including Alzheimer's disease, stroke, status epilepticus and head injury), ischemias (including cerebral ischameia especially acute ischemia, ischemic diseases of the eye), muscle spasms (such as local or general spasticity), autoimmune disorders of the nervous system including paraneoplastic syndromes, spinal muscular atrophy, vomiting, skin disorders and any other disorders associated with irregularities of glutamatergic signal transmission.

Compounds exemplified herein are based around the structure:

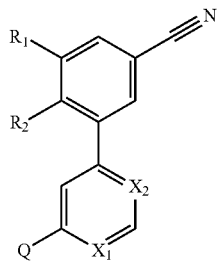
(1)

where $R_1$ is halogen, optionally substituted $C_1$-$C_3$ alkyl, cyclopropyl, optionally substituted $C_1$-$C_3$ alkoxy, cyano, hydroxyl, nitro or $NH_2$;
$R_2$ is H or F;
$X_1$ and $X_2$ are CH or N, where one or both $X_1$ or $X_2$ is N; and
Q is an optionally substituted 5 or 6 membered monocyclic aromatic heterocyclic group.

Compounds may include compounds of formula 2

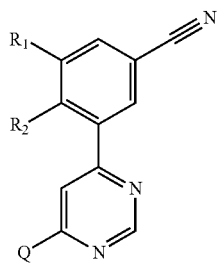
(2)

where $R_1$ is halogen, optionally substituted $C_1$-$C_3$ alkyl, cyclopropyl, optionally substituted $C_1$-$C_3$ alkoxy, cyano, hydroxyl, nitro or $NH_2$;
$R_2$ is H or F; and
Q is an optionally substituted pyridyl or pyrazyl group.

Compounds may include compounds of formula 3

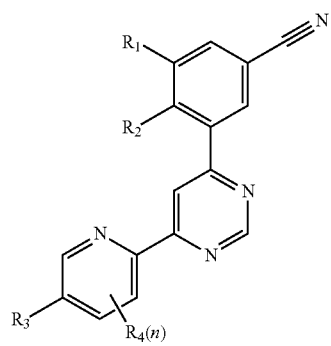
(3)

where $R_1$ is halogen, optionally substituted $C_1$-$C_3$ alkyl, cyclopropyl, optionally substituted $C_1$-$C_3$ alkoxy, cyano, hydroxyl, nitro or $NH_2$;
$R_2$ is H or F;
$R_3$ is H, halogen, optionally substituted $C_1$-$C_3$ alkyl, optionally substituted $C_1$-$C_3$ alkoxy, cyano or a ring N;
$R_4$ is H, halogen, optionally substituted $C_1$-$C_3$ alkyl, optionally substituted $C_1$-$C_3$ alkoxy, cyano or a ring N and n is 0-3. $R_4$ can be 1-3 optional substituents, including ring nitrogen atoms. The further substituents can be any position on the pyridyl ring. Where n is greater than 1, each $R_4$ may be the same or different. Where the substituents are ring nitrogen atoms, n can be 1 or 2. Where the substituents are ring nitrogen atoms, the ring can be further substituted with $R_4$ groups on different carbon atoms. Where $R_4$ is H and n is 3 (or n is 0, and hence $R_4$ is absent), the ring is not further substituted, as formula 4.

Compounds may include compounds of formula 4

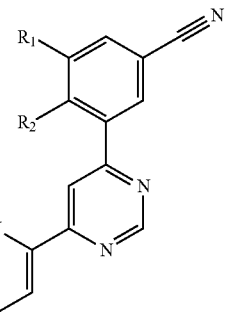
(4)

where $R_1$ is halogen, optionally substituted $C_1$-$C_3$ alkyl, cyclopropyl, optionally substituted $C_1$-$C_3$ alkoxy, cyano, hydroxyl, nitro or $NH_2$;
$R_2$ is H or F; and
$R_3$ is H, halogen, optionally substituted $C_1$-$C_3$ alkyl, optionally substituted $C_1$-$C_3$ alkoxy, cyano or a ring N.

Compounds may include compounds of formula 5

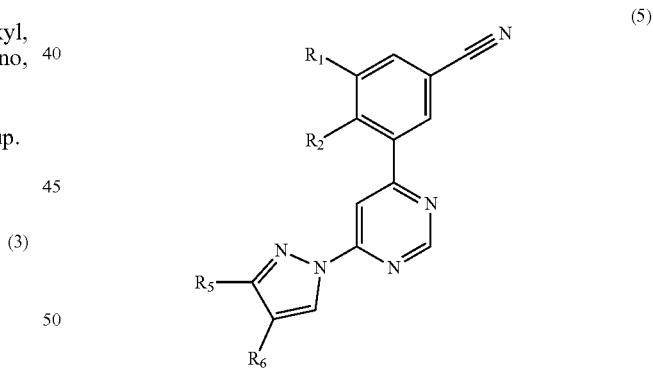
(5)

Where $R_1$ is halogen, optionally substituted $C_1$-$C_3$ alkyl, cyclopropyl, optionally substituted $C_1$-$C_3$ alkoxy, cyano, hydroxyl, nitro or $NH_2$;
$R_2$ is H or F;
$R_5$ is H, D, halogen, optionally substituted $C_1$-$C_3$ alkyl or cyano; and
$R_6$ is H, D, halogen, optionally substituted $C_1$-$C_3$ alkyl or cyano.

Q can be an optionally substituted 5 or 6 membered monocyclic aromatic heterocyclic group. Q can be an aryl or heteroaryl group. In one general embodiment, the substituents for the aryl and heteroaryl groups forming part of Q may be selected from deutero, halo (fluoro, chloro, bromo or iodo), $C_{1-4}$ alkyl, $C_{1-4}$ alkylsulfanyl, $C_{1-4}$ alkylsulfinyl, $C_{1-4}$ alkylsulphonyl, $C_{3-6}$ cycloalkyl, hydroxy, $C_{1-4}$ alkoxy, cyano, nitro, amino, $C_{1-4}$ alkylamino, $C_{2-4}$ alkenylamino, di-$C_{1-4}$ alkylamino, $C_{1-4}$ acylamino, phenyl, phenylamino, benzoylamino, benzylamino, phenylamido, carboxy, $C_{1-4}$ alkoxycarbonyl or phenyl-$C_{1-10}$ alkoxycarbonyl, carbamoyl, mono-$C_{1-4}$ carbamoyl, di-$C_{1-4}$ carbamoyl or any of the above in which a hydrocarbyl moiety is itself substituted by halo, cyano, hydroxy, $C_{1-2}$ alkoxy, amino, nitro, carbamoyl, carboxy or $C_{1-2}$ alkoxycarbonyl.

More particularly, the substituents for the aryl and heteroaryl groups forming part of Q may be selected from deutero, halo (fluoro, chloro, bromo or iodo), $C_{1-4}$ alkyl, $C_{3-6}$ cycloalkyl, hydroxy, $C_{1-4}$ alkoxy, cyano, amino, $C_{1-4}$ alkylamino, di-$C_{1-4}$ alkylamino, $C_{1-4}$ acylamino, carboxy, $C_{1-4}$ alkoxycarbonyl, carbamoyl, mono-$C_{1-4}$ carbamoyl, di-$C_{1-4}$ carbamoyl or any of the above substituents in which a hydrocarbyl moiety is itself substituted by halo, cyano, hydroxy, $C_{1-2}$ alkoxy, amino, nitro, carbamoyl, carboxy or $C_{1-2}$ alkoxycarbonyl.

In a particular embodiment, the substituents for the aryl and heteroaryl groups forming part of Q may be selected from deutero, fluoro, chloro, bromo, $C_{1-3}$ alkyl, $C_{3-6}$ cycloalkyl, hydroxy, $C_{1-4}$ alkoxy, cyano, amino, $C_{1-2}$ alkylamino, di-$C_{1-2}$ alkylamino, $C_{1-2}$ acylamino, carboxy, $C_{1-2}$ alkoxycarbonyl, carbamoyl, mono-$C_{1-2}$ carbamoyl, di-$C_{1-2}$ carbamoyl or any of the above substituents in which a hydrocarbyl moiety is itself substituted by one or more fluorine atoms or by cyano, hydroxy, $C_{1-2}$ alkoxy, amino, carbamoyl, carboxy or $C_{1-2}$ alkoxycarbonyl.

In a more particular embodiment, the substituents for the aryl and heteroaryl groups forming part of Q may be selected from deutero, fluoro, chloro, bromo, cyano, $C_{1-3}$ alkyl and $C_{1-3}$ alkoxy, wherein the $C_{1-3}$ alkyl and $C_{1-3}$ alkoxy moieties are each optionally substituted with one or more fluorine atoms.

The Q group may comprise a substituted aryl or heteroaryl group. In a 6-membered aromatic ring the substituents may be located at the 2, 3, 4, 5 or 6 positions. The aryl or heteroaryl group may comprise one, two, three, four or more substituents. The aryl group may be disubstituted, with the substitutions at any two of positions 2 to 6. The aryl group may be a 2,3-disubstituted, 2,4-disubstituted, 2,5-disubstituted, 2,6-disubstituted, 3,4-disubstituted or 3,5-disubstituted aryl group.

The Q group may be a heteroaryl group, for example 2, 3 or 4 pyridyl. The heteroaryl group may optionally be further substituted, for example 5-fluoro, 2-pyridyl or disubstituted, for example 4,5-difluoro, 2-pyridyl. The heteroaryl group may be 5 or 6 membered, and contain one or more heteroatoms. The heteroaryl group may be a 5 membered ring containing two or more heteroatoms. The heteroatoms may be independently nitrogen, oxygen or sulphur.

Q may be an optionally substituted pyrazyl, pyridyl, oxazyl, thiazyl or diazinyl. Q may be selected from optionally substituted rings of formula (a)

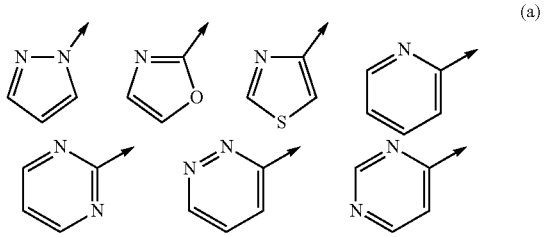

(a)

$X_1$ and $X_2$ can be CH or N. In particular examples, either $X_1$ or $X_2$ is N. In particular examples both $X_1$ and $X_2$ are N.

Where $R_1$ can be halogen, optionally substituted $C_1$-$C_3$ alkyl, cyclopropyl, optionally substituted $C_1$-$C_3$ alkoxy, cyano, hydroxyl, nitro or $NH_2$. $R_1$ is not H, and hence $R_1$ must be substituted with an atom other than H. $R_1$ can be F. $R_1$ can be Cl. $R_1$ can be methyl or substituted methyl, for example methoxymethyl, fluoromethyl, difluoromethyl or trifluoromethyl. $R_1$ can be methoxy or substituted methoxy, for example fluoromethoxy, difluoromethoxy or trifluoromethoxy. $R_1$ can be optionally substituted cyclopropyl. $R_1$ can be cyano. The optional substituents may consist of one or more halo, alkyl or alkoxy groups, or may be selected from the list of optional substituents shown below.

$R_2$ can be H or F. $R_2$ can be H. $R_2$ can be F.

$R_3$ can be H, halogen, optionally substituted $C_1$-$C_3$ alkyl, optionally substituted $C_1$-$C_3$ alkoxy, cyano or a ring N. $R_3$ can be H. $R_3$ can be D. $R_3$ can be F. $R_3$ can be Cl. $R_3$ can be a ring nitrogen. $R_3$ can be methyl or substituted methyl, for example methoxymethyl, fluoromethyl, difluoromethyl or trifluoromethyl. $R_3$ can be cyano. The optional substituents may consist of one or more halo, alkyl or alkoxy groups, or may be selected from the list of optional substituents shown below.

$R_4$ can be H, halogen, optionally substituted $C_1$-$C_3$ alkyl, optionally substituted $C_1$-$C_3$ alkoxy, cyano or a ring N. $R_4$ can be H. $R_4$ can be D. $R_4$ can be F. $R_4$ can be Cl. $R_4$ can be a ring nitrogen. $R_4$ can be methyl or substituted methyl, for example methoxymethyl, fluoromethyl, difluoromethyl or trifluoromethyl. $R_4$ can be cyano. The optional substituents may consist of one or more halo, alkyl or alkoxy groups, or may be selected from the list of optional substituents shown below.

$R_5$ can be H, halogen, optionally substituted $C_1$-$C_3$ alkyl or cyano. $R_5$ can be H. $R_5$ can be D. $R_5$ can be F. $R_5$ can be Cl. $R_5$ can be methyl or substituted methyl, for example methoxymethyl, fluoromethyl, difluoromethyl or trifluoromethyl. The optional substituents may consist of one or more halo, alkyl or alkoxy groups, or may be selected from the list of optional substituents shown below.

$R_6$ can be H, halogen, optionally substituted $C_1$-$C_3$ alkyl or cyano. $R_6$ can be H. $R_6$ can be D. $R_6$ can be F. $R_6$ can be Cl. $R_6$ can be methyl or substituted methyl, for example methoxymethyl, fluoromethyl, difluoromethyl or trifluoromethyl. The optional substituents may consist of one or more halo, alkyl or alkoxy groups, or may be selected from the list of optional substituents shown below.

Any of the features of $R_1$-$R_6$, Q, $X_1$ and $X_2$ defined herein may be combined with any of the other features of $R_1$-$R_6$, Q, $X_1$ and $X_2$. Certain specific examples of compounds are shown below.

Further embodiments of the invention include methods of treatment comprising administering a compound of formulas 1-5 as mGlu5 modulators. The treatment using a compound of formulas 1-5 may be in the treatment of dementia (including senile dementia and dementia caused by AIDS), pain (including headaches (such as migraine and cluster headaches), inflammatory pain (such as inflammatory tongue pain), visceral pain syndromes (such as painful bladder syndrome), gastro-intestinal pain (including irritable bowel syndrome), itch, fibromyalgia), disorders of the urinary tract (including incontinence, prostatitis, urinary frequency, nocturia, overactive bladder, cystitis, benign prostatic hyperplasia, detrusor hyperreflexia, outlet obstruction, urinary urgency, pelvic hypersensitivity, urge incontinence, urethritis, prostatodynia, idiopathic bladder hypersensitivity), substance-related disorders (including addiction, alcohol abuse, alcohol dependence, alcohol withdrawal, amphetamine dependence, amphetamine withdrawal, cocaine dependence, cocaine withdrawal, opioid dependence, opioid withdrawal), anxiety disorders (including agoraphobia, generalized anxiety disorder (GAD), obsessive compulsive disorder (OCD), panic disorder, post-traumatic stress disorders, social and specific phobias, substance-induced anxiety disorder), eating disorders (including obesity, anorexia and bulimia), attention-deficit/hyperactivity disorder (ADHD; ADD), deficits and abnormalties in attention and vigilance, executive functions and memory, movement disorders (including Parkinson's disease, levodopa-induced dyskinesias, Tourette's syndrome, Huntington's disease, dystonias, restless leg syndrome, simple tics, complex tics and symptomatic tics, periodic limb movement syndromes), amyotrophic lateral sclerosis (ALS), multiple sclerosis, schizophrenia, cancer (including melanoma, squamous cell carcinoma and astrocytoma), mood disorders (including major depressive disorder, dysthymia, treatment-resistant depression and bipolar disorders I and II), rare neurological diseases including inherited diseases and developmental disorders (including autistic spectrum disorders [Asperger's syndrome, Rett's syndrome, Pervasive Development Disorder Not Otherwise Specified, Childhood Disintegrative Disorder] and Down's syndrome), fragile X syndrome and other areas of mental retardation, disorders of the gastro-intestinal tract (including gastroesophageal reflux disease, functional dyspepsia, functional heartburn, irritable bowel syndrome, functional bloating, functional diarrhoea, chronic constipation, post-operative ileus), epilepsy, retinopathy, neuroprotection (including Alzheimer's disease, stroke, status epilepticus and head injury), ischemias (including cerebral ischameia especially acute ischemia, ischemic diseases of the eye), muscle spasms (such as local or general spasticity), autoimmune disorders of the nervous system including paraneoplastic syndromes, spinal muscular atrophy, vomiting, skin disorders and any other disorders associated with irregularities of glutamatergic signal transmission. The methods of treatment will typically involve the administration of a therapeutically effective amount (preferably a non-toxic amount) of the compound to a subject (e.g. a mammalian subject such as a human) in need thereof.

Certain novel compounds of the invention show particularly high activities as mGlu5 negative allosteric modulators; for example 3-chloro-4-fluoro-5-[6-(pyridin-2-yl)pyrimidin-4-yl]benzonitrile
3-chloro-5-[6-(pyridin-2-yl)pyrimidin-4-yl]benzonitrile
6-[6-(3-chloro-5-cyanophenyl)pyrimidin-4-yl]pyridine-3-carbonitrile
3-methyl-5-[6-(pyridin-2-yl)pyrimidin-4-yl]benzonitrile
3-chloro-5-[6-(pyridazin-3-yl)pyrimidin-4-yl]benzonitrile
3-(4,4'-bipyrimidin-6-yl)-5-chlorobenzonitrile
3-methyl-5-[6-(1H-pyrazol-1-yl)pyrimidin-4-yl]benzonitrile
3-chloro-5-[6-(1H-pyrazol-1-yl)pyrimidin-4-yl]benzonitrile
3-chloro-4-fluoro-5-[6-(1H-pyrazol-1-yl)pyrimidin-4-yl]benzonitrile
3-chloro-4-fluoro-5-[4-(1H-pyrazol-1-yl)pyridin-2-yl]benzonitrile
3-chloro-4-fluoro-5-[2-(1H-pyrazol-1-yl)pyridin-4-yl]benzonitrile
3-chloro-4-fluoro-5-[6-(4-fluoro-1H-pyrazol-1-yl)pyrimidin-4-yl]benzonitrile
3-methyl-5-{6-[($^2$H$_3$)-1H-pyrazol-1-yl]pyrimidin-4-yl}benzonitrile
3-chloro-5-{6-[($^2$H$_3$)-1H-pyrazol-1-yl]pyrimidin-4}-yl benzonitrile
3-chloro-4-fluoro-5-{6-[($^2$H$_3$)-1H-pyrazol-1-yl]pyrimidin-4-yl}benzonitrile
3-(fluoromethyl)-5-[6-(1H-pyrazol-1-yl)pyrimidin-4-yl]benzonitrile
3-chloro-5-[6-(5-fluoropyridin-2-yl)pyrimidin-4-yl]benzonitrile
5-[6-(5-fluoropyridin-2-yl)pyrimidin-4-yl]benzene-1,3-dicarbonitrile
3-chloro-5-[6-(5-methylpyridin-2-yl)pyrimidin-4-yl]benzonitrile
3-chloro-5-[6-(5-chloropyridin-2-yl)pyrimidin-4-yl]benzonitrile
5-[6-(pyridin-2-yl)pyrimidin-4-yl]benzene-1,3-dicarbonitrile
3-chloro-4-fluoro-5-[6-(5-fluoropyridin-2-yl)pyrimidin-4-yl]benzonitrile
3-methyl-5-[6-(5-methylpyridin-2-yl)pyrimidin-4-yl]benzonitrile
3-[6-(5-fluoropyridin-2-yl)pyrimidin-4-yl]-5-(methoxymethyl)benzonitrile
3-[6-(5-fluoropyridin-2-yl)pyrimidin-4-yl]-5-methoxybenzonitrile To the extent that any of the compounds described have chiral centres, the present invention extends to all optical isomers of such compounds, whether in the form of racemates or resolved enantiomers. The invention described herein relates to all crystal forms, solvates and hydrates of any of the disclosed compounds however so prepared. To the extent that any of the compounds disclosed herein have acid or basic centres such as carboxylates or amino groups, then all salt forms of said compounds are included herein. In the case of pharmaceutical uses, the salt should be seen as being a pharmaceutically acceptable salt.

Pharmaceutically acceptable salts that may be mentioned include acid addition salts and base addition salts. Such salts may be formed by conventional means, for example by reaction of a free acid or a free base form of a compound with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound in the form of a salt with another counter-ion, for example using a suitable ion exchange resin.

Examples of pharmaceutically acceptable salts include acid addition salts derived from mineral acids and organic acids, and salts derived from metals such as sodium, magnesium, or preferably, potassium and calcium.

Examples of acid addition salts include acid addition salts formed with acetic, 2,2-dichloroacetic, adipic, alginic, aryl sulfonic acids (e.g. benzenesulfonic, naphthalene-2-sulfonic, naphthalene-1,5-disulfonic and p-toluenesulfonic), ascorbic (e.g. L-ascorbic), L-aspartic, benzoic, 4-acetamidobenzoic, butanoic, (+)-camphoric, camphor-sulfonic, (+)-(1S)-camphor-10-sulfonic, capric, caproic, caprylic, cinnamic, citric, cyclamic, dodecyl sulfuric, ethane-1,2-disulfonic, ethanesulfonic, 2-hydroxyethanesulfonic, formic, fumaric, galactaric, gentisic, glucoheptonic, gluconic (e.g. D-gluconic), glucuronic (e.g. D-glucuronic), glutamic (e.g. L-glutamic), α-oxoglutaric, glycolic, hippuric, hydrobromic, hydrochloric, hydriodic, isethionic, lactic (e.g. (+)-L-lactic and (±)-DL-lactic), lactobionic, maleic, malic (e.g. (−)-L-malic), malonic, (±)-DL-mandelic, metaphosphoric, methanesulfonic, 1-hydroxy-2-naphthoic, nicotinic, nitric, oleic, orotic, oxalic, palmitic, pamoic, phosphoric, propionic, L-pyroglutamic, salicylic, 4-amino-salicylic, sebacic, stearic, succinic, sulfuric, tannic, tartaric (e.g. (+)-L-tartaric), thiocyanic, undecylenic and valeric acids.

Particular examples of salts are salts derived from mineral acids such as hydrochloric, hydrobromic, phosphoric, meta-phosphoric, nitric and sulfuric acids; from organic acids, such as tartaric, acetic, citric, malic, lactic, fumaric, benzoic, glycolic, gluconic, succinic, arylsulfonic acids; and from metals such as sodium, magnesium, or preferably, potassium and calcium.

Also encompassed are any solvates of the compounds and their salts. Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulfoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGE), differential scanning calorimetry (DSC) and X-ray crystallography.

The solvates can be stoichiometric or non-stoichiometric solvates. Particular solvates may be hydrates, and examples of hydrates include hemihydrates, monohydrates and dihydrates.

For a more detailed discussion of solvates and the methods used to make and characterise them, see Bryn et al., Solid-State Chemistry of Drugs, Second Edition, published by SSCI, Inc of West Lafayette, Ind., USA, 1999, ISBN 0-967-06710-3.

"Pharmaceutically functional derivatives" of compounds as defined herein includes ester derivatives and/or derivatives that have, or provide for, the same biological function and/or activity as any relevant compound of the invention. Thus, for the purposes of this invention, the term also includes prodrugs of compounds as defined herein.

The term "prodrug" of a relevant compound includes any compound that, following oral or parenteral administration, is metabolised in vivo to form that compound in an experimentally-detectable amount, and within a predetermined time (e.g. within a dosing interval of between 6 and 24 hours (i.e. once to four times daily)).

Prodrugs of compounds may be prepared by modifying functional groups present on the compound in such a way that the modifications are cleaved, in vivo when such prodrug is administered to a mammalian subject. The modifications typically are achieved by synthesizing the parent compound with a prodrug substituent. Prodrugs include compounds wherein a hydroxyl, amino, sulfhydryl, carboxyl or carbonyl group in a compound is bonded to any group that may be cleaved in vivo to regenerate the free hydroxyl, amino, sulfhydryl, carboxyl or carbonyl group, respectively.

Examples of prodrugs include, but are not limited to, esters and carbamates of hydroxyl functional groups, ester groups of carboxyl functional groups, N-acyl derivatives and N-Mannich bases. General information on prodrugs may be found e.g. in Bundegaard, H. "Design of Prodrugs" p. 1-92, Elsevier, New York-Oxford (1985).

Definitions $C_1$-$C_3$ Alkyl

Alkyl means an aliphatic hydrocarbon group. The alkyl group may be straight or branched. "Branched" means that at least one carbon branch point is present in the group, for example isopropyl. $C_1$-$C_3$ alkyl groups include methyl, ethyl, n-propyl, i-propyl. The alkyl group may be optionally substituted, e.g. as exemplified below.

The term alkyl also includes aliphatic hydrocarbon groups such as alkenyl, and alkylidene.

Alkenyl

Alkenyl means an unsaturated aliphatic hydrocarbon group. The unsaturation may include one or more double bond, one or more triple bond or any combination thereof. The alkenyl group may be straight or branched. "Branched" means that at least one carbon branch point is present in the group. Any double bond may, independently of any other double bond in the group, be in either the (E) or the (Z) configuration. $C_1$-$C_3$ alkenyl groups include ethenyl, n-propenyl, i-propenyl. Where alternative (E) and (Z) forms are possible, each is to be considered as individually identified. The alkenyl group may be optionally substituted, e.g. as exemplified below.

Alkylidene

Alkylidene means any alkyl or alkenyl group linked to the remainder of the molecule via a double bond. The definitions and illustrations provided herein for alkyl and alkenyl groups apply with appropriate modification also to alkylidene groups.

$C_1$-$C_3$ Alkyloxy

Alkoxy means an aliphatic hydrocarbon group linked via an oxygen atom. The alkyl group may be straight or branched. "Branched" means that at least one carbon branch point is present in the group, for example isopropyl. $C_1$-$C_3$ alkoxy groups include methoxy, ethoxy, n-propoxy, i-propoxy. The alkoxy group may be optionally substituted, e.g. as exemplified below.

Aryl

Aryl means any aromatic group in which all of the ring members are carbon atoms, for example having 6 carbon atom ring members (phenyl).

Heteroaryl

Heteroaryl means an aromatic group in which at least one ring member is other than carbon. For example, at least one ring member (for example one, two or three ring members) may be selected from nitrogen, oxygen and sulphur. Exemplary heteroaryl groups include pyrazyl, pyridyl, oxazyl, thiazyl or diazinyl.

Optionally Substituted

"Optionally substituted" as applied to any group means that the said group may if desired be substituted with one or more substituents, which may be the same or different. Examples of suitable substituents for "substituted" and "optionally substituted" moieties include halo (fluoro, chloro, bromo or iodo), deutero, $C_{1-3}$ alkyl, hydroxy, $C_{1-3}$ alkoxy, cyano, amino, nitro, $C_{1-3}$ alkylamino, $C_{2-6}$ alkenylamino, di-$C_{1-3}$alkylamino, $C_{1-3}$ acylamino, di-$C_{1-3}$ acylamino, carboxy, $C_{1-3}$ alkoxycarbonyl, carbamoyl, mono-$C_{1-3}$ carbamoyl, di-$C_{1-3}$ carbamoyl or any of the above in which a hydrocarbyl moiety is itself substituted by halo, cyano, hydroxy, $C_{1-2}$ alkoxy, amino, nitro, carbamoyl, carboxy or $C_{1-2}$ alkoxycarbonyl. In groups containing an oxygen atom such as hydroxy and alkoxy, the oxygen atom can be replaced with sulphur to make groups such as thio (SH) and thio-alkyl (S-alkyl). Optional substituents therefore includes groups such as S-methyl. In thio-alkyl groups, the sulphur atom may be further oxidised to make a sulfoxide or sulfone, and thus optional substituents therefore includes groups such as S(O)-alkyl and S(O)$_2$-alkyl.

Substituted groups thus include for example CN, CFH$_2$, CF$_2$H, CF$_3$, CH$_2$NH$_2$, CH$_2$OH, CH$_2$CN, CH$_2$SCH$_3$, CH$_2$OCH$_3$, OMe, OEt, Me, Et, —OCH$_2$O—, CO$_2$Me, C(O)Me, i-Pr, SCF$_3$, SO$_2$Me, NMe$_2$ etc. In the case of aryl groups, the substitutions may be in the form of rings from adjacent carbon atoms in the aryl ring, for example cyclic acetals such as O—CH$_2$—O.

"Acyl" means an H—CO— or C$_{1-3}$ alkyl-CO— group wherein the alkyl group is as defined herein. Exemplary acyl groups include formyl, acetyl, propanoyl and 2-methylpropanoyl.

The term "pharmaceutical composition" in the context of this invention means a composition comprising an active agent and comprising additionally one or more pharmaceutically acceptable carriers. The composition may further contain ingredients selected from, for example, diluents, adjuvants, excipients, vehicles, preserving agents, fillers, disintegrating agents, wetting agents, emulsifying agents, suspending agents, sweetening agents, flavouring agents, perfuming agents, antibacterial agents, antifungal agents, lubricating agents and dispersing agents, depending on the nature of the mode of administration and dosage forms. The compositions may take the form, for example, of tablets, dragees, powders, elixirs, syrups, liquid preparations including suspensions, sprays, inhalants, tablets, lozenges, emulsions, solutions, cachets, granules, capsules and suppositories, as well as liquid preparations for injections, including liposome preparations.

The dosages may be varied depending upon the requirements of the patient, the severity of the condition being treated, and the compound being employed. Determination of the proper dosage for a particular situation is within the skill of the art. Generally, treatment is initiated with the smaller dosages which are less than the optimum dose of the compound. Thereafter the dosage is increased by small increments until the optimum effect under the circumstances is reached. For convenience, the total daily dosage may be divided and administered in portions during the day if desired.

The magnitude of an effective dose of a compound will, of course, vary with the nature of the severity of the condition to be treated and with the particular compound and its route of administration. The selection of appropriate dosages is within the ability of one of ordinary skill in this art, without undue burden. In general, the daily dose range may be from about 10 μg to about 30 mg per kg body weight of a human and non-human animal, preferably from about 50 μg to about 30 mg per kg of body weight of a human and non-human animal, for example from about 50 μg to about 10 mg per kg of body weight of a human and non-human animal, for example from about 100 μg to about 30 mg per kg of body weight of a human and non-human animal, for example from about 100 μg to about 10 mg per kg of body weight of a human and non-human animal and most preferably from about 100 μg to about 1 mg per kg of body weight of a human and non-human animal.

SYNTHESIS OF EXAMPLES

Preparation of the Compounds of the Invention

Compounds of the invention may be prepared by routes including those in FIG. 1, where in each case the starting aromatic or heteroaromatic ring may be optionally substituted by groups in addition to those shown. Details of many of the standard transformations such as those in the routes below and others which could be used to perform the same transformations can be found in standard reference textbooks such as "Organic Synthesis", M. B. Smith, McGraw-Hill (1994) or "Advanced Organic Chemistry", 4$^{th}$ edition, J. March, John Wiley & Sons (1992).

Heteroaryl trialkylstanannes, where the alkyl group is commonly methyl or n-butyl, can be formed from the corresponding heteroaryl halide, for example the bromide (for example as in Route 1, Step 1 or Route 4, where heteroaryl trialkylstannanes can be synthesized for use in step 2). Conversion to the trialkylstannane can be performed under palladium mediated cross-coupling conditions, using a suitable palladium(0) catalyst, for example tetrakis(triphenylphosphine)palladium(0), in a suitable solvent such as DME, typically at an elevated temperature, for example 80-110° C. Additionally a number of heteroaryl trilkylstannanes are available commercially. Cross-coupling of a heteroaryl trialkylstannane with a heteroaryl halide (for example in Route 1, Step 2 or Route 4, Step 2), for example a chloropyrimidine, can be undertaken under palladium mediated Stille cross-coupling conditions which will be known to those skilled in the art. For example, Stille couplings can be undertaken using a suitable palladium(0) catalyst, for example tetrakis(triphenylphosphine) palladium (0), a copper(I) salt, for example copper(I) iodide, in a suitable solvent such as toluene, typically at an elevated temperature, for example 110° C. An alternative to the use of the Stille cross-coupling procedure is the Negishi cross-coupling reaction (Negishi et al, *J.C.S. Chem. Comm.*, 1977, 683-684) which couples an organozinc compound with an aryl halide or heteroaryl halide (for example in Route 5, Step 2), using a suitable palladium catalyst, for example tetrakis (triphenylphosphine) palladium(0), in a suitable solvent such as THF, typically at an elevated temperature, for example 50-60° C. Organozinc compounds can be prepared by methods which will be known to those skilled in the art, for example by treatment of an aryl halide or heteroaryl halide with iso-propylmagnesium chloride in THF, followed by treatment with zinc(II) chloride.

Compounds may be prepared by reacting compounds of formula X:

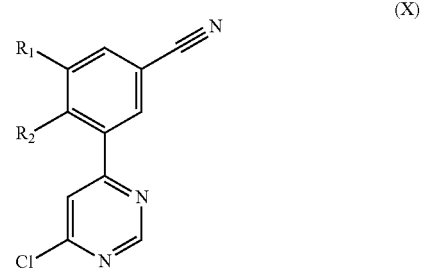

(X)

where R$_1$ is halogen, optionally substituted C$_1$-C$_3$ alkyl, cyclopropyl, optionally substituted C$_1$-C$_3$ alkoxy, cyano, hydroxyl, nitro or NH$_2$; and R$_2$ is H or F;

with a 2-pyridyl stannane reagent (Stille coupling) or 2-pyridyl organozinc reagent (Negishi coupling) to form an aryl-aryl bond.

Aryl or heteroarylboronic acids or esters, for example pinacol esters, can be used in the preparation of compounds of the invention, for example in Route 1, Step 3; Route 2, Step 3; Route 3, Step 2, Route 4, Step 1 and Route 5, Step 1. Many aryl or heteroarylboronic acids or esters are commercially available. In addition, conditions which will be known to those skilled in the art can be used for their synthesis. For example, halogen-lithium exchange, typically using an organolithium reagent such as n-BuLi, can be used to form an aryl or heteroaryl lithium nucleophile from an aryl or heteroarylhalide at low temperature, typically −78° C. in an inert solvent such as THF, which can subsequently be reacted with a trialkylborate such as triisopropyl borate to form an aryl or heteroarylboronic acid after aqueous workup. Aryl or heteroarylboronic pinacol esters can be formed directly from aryl or heteroaryl compounds via iridium-catalysed C—H borylation using methods which are known to those skilled in the art, for example as reviewed by Hartwig et al, Chem. Rev. 2010, 110, 890-931. One such method, for example as described in Steel et al, Org. Lett. 2009, 11, 3586-3589, uses an iridium catalyst such as (1,5-cyclooctadiene)(methoxy) iridium(I) dimer, a ligand such as 4,4'-di-tert-butyl-2,2'-dipyridyl and bis(pinacolato) diboron in a suitable solvent such as TBME, at a suitable temperature, for example 80° C., under conventional or microwave heating conditions. Cross-coupling of an aryl or heteroarylboronic acid or ester with a heteroaryl halide, for example a chloropyrimidine, chloropyridine or a bromopyridine, can be undertaken under palladium mediated Suzuki cross-coupling conditions which will be known to those skilled in the art (for example in Route 1, Step 3; Route 2, Step 3; Route 3, Step 2 or Route 4, Step 1). For example, Suzuki couplings can be undertaken using a suitable palladium catalyst, for example [1,1'-bis(diphenylphosphino)ferrocene]dichloropalladium(II) or the complex of this catalyst with dichloromethane, and a base, for example cesium carbonate or sodium carbonate, in a suitable solvent or solvent mixture, such as 1,4-dioxane or a mixture of 1,4-dioxane and water, typically at an elevated temperature, for example 80-100° C.

A number of heterocycle-substituted chloro- or bromopyrimidines or chloro- or bromopyridines are commercially available, for examples Intermediates 34, 35 and 36. In addition, conditions which will be known to those skilled in the art can be used for their synthesis. One such method (for example Route 2) converts a heterocyclic carboxylic acid, via the acid chloride, to the corresponding beta ketoester using the anion of ethyl acetate. Subsequent condensation with formamidine hydrochloride under basic conditions, for example in the presence of sodium methoxide in methanol at rt, can be used to form a hydroxyl substituted pyrimidine, which can be converted to the chloropyrimidine under standard conditions, for example using phosphorous(V) oxychloride. Other methods for the synthesis of heterocycle-substituted chloropyrimidines or pyridines include those described above, palladium(0) catalysed Stille or Suzuki cross couplings. A further method of the synthesis of a heterocycle-substituted chloropyrimidine uses the nucleophilic aromatic substitution reaction ($S_NAr$) (for example Route 3, Step 1). In the synthesis of compounds of the invention $S_NAr$ reactions are typically conducted at 0° C. or rt, in a suitable solvent such as DMF, and in the presence of a suitable base such as potassium carbonate.

General Procedures

Where no preparative routes are included, the relevant intermediate is commercially available. Commercial reagents were utilized without further purification. Room temperature (rt) refers to approximately 20-27° C. $^1$H NMR spectra were recorded at 400 MHz on Bruker, Varian or JEOL instruments. Chemical shift values are expressed in parts per million (ppm), i.e. (δ)-values. The following abbreviations are used for the multiplicity of the NMR signals: s=singlet, br=broad, d=doublet, t=triplet, q=quartet, quin=quintet, h=heptet, dd=doublet of doublets, dt=double of triplets, m=multiplet. Coupling constants are listed as J values, measured in Hz. NMR and mass spectroscopy results were corrected to account for background peaks. Chromatography refers to column chromatography performed using 60-120 mesh silica gel and executed under nitrogen pressure (flash chromatography) conditions. TLC for monitoring reactions refers to TLC run using the specified mobile phase and silica gel F254 as a stationary phase from Merck. Microwave-mediated reactions were performed in Biotage Initiator or CEM Discover microwave reactors.

LCMS experiments were carried out using electrospray conditions under the following conditions. Instruments: Waters Alliance 2795, Waters 2996 PDA detector, Micromass ZQ (or Hewlett Packard 1100 with G1315A DAD, Micromass ZQ for examples 24 and 25); Column: Waters X-Bridge C-18, 2.5 micron, 2.1×20 mm or Phenomenex Gemini-NX C-18, 3 micron, 2.0×30 mm; Gradient [time (min)/solvent D in C (%)]:0.00/2, 0.10/2, 8.40/95, 9.40/95; Solvents: solvent C=2.5 L $H_2O$+2.5 mL 28% ammonia in water solution; solvent D=2.5 L MeCN+135 mL $H_2O$+2.5 mL 28% ammonia in water solution); Injection volume 3 μL (or 1 μL for examples 24 and 25); UV detection 230 to 400 nM; column temperature 45° C.; Flow rate 1.5 mL/min. LCMS data in the experimental section are given in the format: Mass ion, retention time, approximate purity.

Abbreviations

DMAC=N,N-dimethylacetamide
DME=1,2-dimethoxyethane
DMF=dimethylformamide
DMSO=dimethylsulfoxide
ES=electrospray
EtOAc=ethyl acetate
h=hour(s)
HPβCD=(2-hydroxypropyl)-β-cyclodextrin
L=Litre
LC=liquid chromatography
LDA=lithium diisopropylamide
MeCN=acetonitrile
min=minute(s)
MS=mass spectrometry
NMR=nuclear magnetic resonance
rt=room temperature
$S_NAr$=nucleophilic aromatic substitution reaction
TBME=tert-butyl methyl ether
THF=tetrahydrofuran
TLC=thin layer chromatography Prefixes n-, s-, i-, t- and tert- have their usual meanings: normal, secondary, iso, and tertiary.

Synthesis of Intermediates

Route 1

Typical Procedure for the Preparation of Intermediates Via Stille Coupling of Commercially Available Trialkylstannanes with 4,6-Dichloropyrimidine as Exemplified by the Preparation of Intermediate 1, 4-chloro-6-(pyridin-2-yl)pyrimidine.

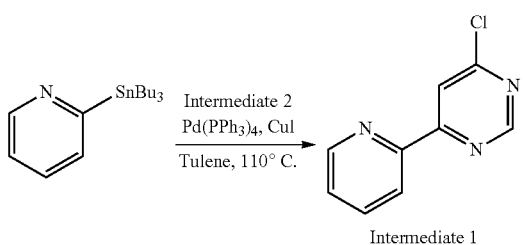

Intermediate 1

A mixture of 4,6-dichloropyrimidine (Intermediate 2, 1.2 g, 8.1 mmol) and 2-(tributylstannyl)pyridine (Intermediate 3, 3.0 g, 8.1 mmol) in toluene (10 mL) was degassed by purging with N₂ for 5 min. Tetrakis(triphenylphosphine)palladium(0) (940 mg, 0.81 mmol) and copper(I) iodide (155 mg, 0.81 mmol) were added and the reaction mixture was stirred at 110° C. for 16 h. After cooling to rt the reaction mixture was partitioned between H₂O (250 mL) and EtOAc (100 mL) and the phases were separated. The aqueous phase was extracted with EtOAc (2×100 mL) and the combined organic phases were dried (Na₂SO₄) and concentrated in vacuo. Purification by gradient flash chromatography, eluting with 0-10% EtOAc in hexane yielded the title compound (310 mg, 1.62 mmol) as a white solid.

Data in table 1.

Typical Procedure for the Preparation of Intermediates Via Synthesis of a Trialkylstannane from the Corresponding Heteroaryl Halide Followed by Stille Coupling as Exemplified by the Preparation of Intermediate 4, 6-(6-chloropyrimidin-4-yl)pyridine-3-carbonitrile.

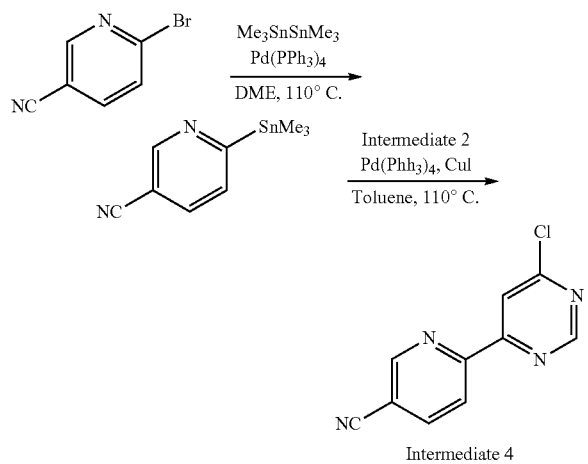

Intermediate 4

A mixture of 2-bromo-5-cyanopyridine (Intermediate 5, 1.07 g, 5.85 mmol) and hexamethylditin (1.21 mL, 5.84 mmol) in DME (10 mL) was degassed by purging with N₂ for 5 min. Tetrakis(triphenylphosphine)palladium(0) (330 mg, 0.29 mmol) was added and the reaction mixture was stirred at 110° C. for 16 h before cooling to rt and partitioning between H₂O (50 mL) and EtOAc (25 mL). The phases were separated and the aqueous phase extracted with EtOAc (2×25 mL). The combined organic phases were dried (Na₂SO₄) and concentrated in vacuo to yield crude 6-(trimethylstannyl)nicotinonitrile (950 mg) as a brown liquid which was used in the subsequent step without characterisation or further purification.

4,6-Dichloropyrimidine (Intermediate 2, 500 mg, 3.36 mmol) and crude 6-(trimethylstannyl)nicotinonitrile (895 mg) were dissolved in toluene (15 mL) and the reaction mixture was degassed by purging with N₂ for 5 min. Tetrakis(triphenylphosphine)palladium(0) (388 mg, 0.34 mmol) and copper iodide (64 mg, 0.33 mmol) were added and the reaction mixture was stirred at 110° C. for 16 h. After cooling to rt, the reaction mixture was partitioned between H₂O (50 mL) and EtOAc (25 mL), the phases were separated and the aqueous phase was extracted with EtOAc (2×25 mL). The combined organic phases were dried (Na₂SO₄) and concentrated in vacuo. Purification by gradient flash chromatography, eluting with 0-10% EtOAc in hexane yielded the title compound (175 mg, 0.81 mmol) as a light yellow solid.

Data in table 1.

Intermediate 6,
3-(6-chloropyrimidin-4-yl)pyridazine

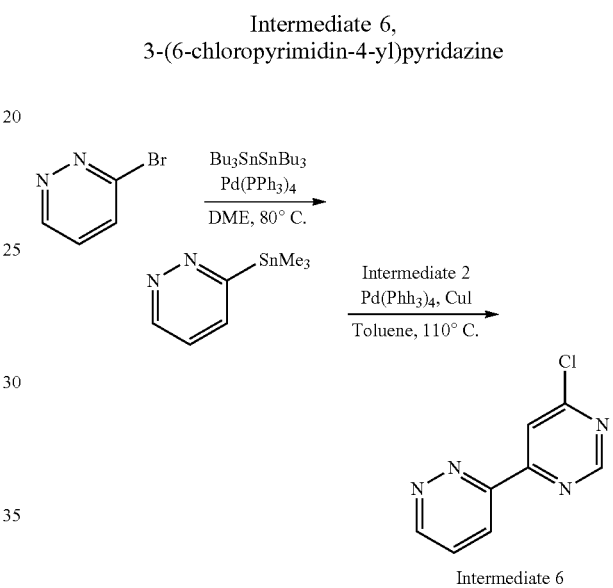

Intermediate 6

The title compound (250 mg, 1.30 mmol) was prepared in two steps from 3-bromopyridazine (Intermediate 7, 500 mg, 3.14 mmol), hexabutylditin (1.23 mL, 2.43 mmol) and 4,6-dichloropyrimidine (Intermediate 2, 300 mg, 2.01 mmol) using the methods of Intermediate 4.

Data in table 1.

Route 2

Typical Procedure for the Preparation of Intermediates Via Pyrimidine Ring Formation from Heteroaryl Carboxylic Acids as Exemplified by the Preparation of Intermediate 8, 6-Chloro-4,4'-Bipyrimidine.

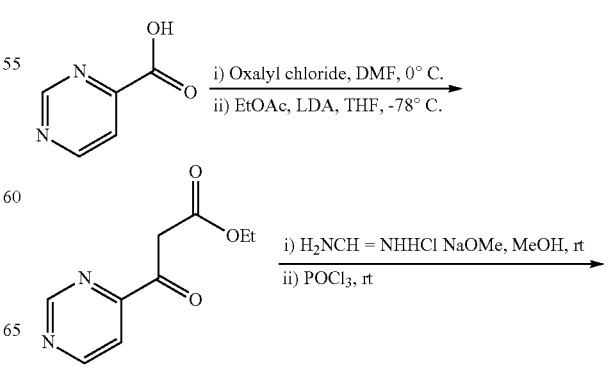

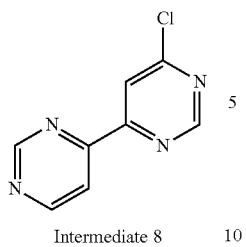

Intermediate 8

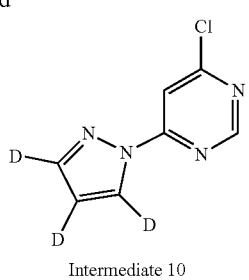

Intermediate 10

4-Pyrimidinecarboxylic acid (Intermediate 9, 3.0 g, 24.2 mmol) in DMF (0.01 mL) and $CH_2Cl_2$ (60 mL) was cooled to 0° C. before the dropwise addition over 10 min of oxalyl chloride (2.7 mL, 31.5 mmol). After stirring at rt for 2 h the reaction mixture was concentrated in vacuo and the resulting crude acid chloride redissolved in THF (10 mL). Separately, EtOAc (8.3 mL, 84.6 mmol) was dissolved in THF (30 mL) and cooled to −78° C. before the dropwise addition of LDA (36.0 mL of a 2 M solution in THF, 72.0 mmol). After stirring at −78° C. for 1 h the THF solution of the crude acid chloride was added and the mixture stirred at −78° C. for 3 h. Aqueous HCl (1N, 25 mL) was added, followed by $H_2O$ (100 mL) and EtOAc (100 mL), and the phases were separated. The aqueous phase was extracted with EtOAc (3×100 mL) and the combined organic phases were dried ($Na_2SO_4$) and concentrated in vacuo. Purification by gradient flash chromatography, eluting with 0-8% EtOAc in hexane yielded ethyl 3-oxo-3-(pyrimidin-4-yl)propanoate (0.40 g, 2.06 mmol) as a white solid.

TLC: Rf 0.6, Hexane/Ethyl acetate 4:1

Ethyl 3-oxo-3-(pyrimidin-4-yl)propanoate (1.2 g, 6.18 mmol), sodium methoxide (1.33 g, 24.6 mmol) and formamidine hydrochloride (1.0 g, 12.4 mmol) were dissolved in MeOH (20 mL) and stirred at room temperature for 24 h before concentration in vacuo. $H_2O$ (50 mL) and EtOAc (50 mL) were added and the phases were separated. The aqueous phase was extracted with EtOAc (3×50 mL) and the combined organic phases were dried ($Na_2SO_4$), and concentrated in vacuo to yield crude [4,4'-bipyrimidin]-6-ol (200 mg) which was used in the next step without further purification.

TLC: Rf 0.1, Ethyl acetate

Crude [4,4'-Bipyrimidin]-6-ol (120 mg, 0.69 mmol) was dissolved in phosphorus(V) oxychloride (4.0 mL, 42.9 mmol) and stirred at rt for 14 h. The mixture was neutralized to approximately pH 7 with saturated aqueous $NaHCO_3$ solution (30 mL) at 0° C. and stirred for 15 min before the addition of EtOAc (300 mL) and $H_2O$ (100 mL). The phases were separated, the aqueous phase was extracted with EtOAc (300 mL), and the combined organic phases were dried ($Na_2SO_4$) and concentrated in vacuo. Purification by gradient flash chromatography, eluting with 0-9% EtOAc in hexane yielded the title compound (42 mg, 0.22 mmol) as a white solid.

Data in table 1.

Route 3

Typical Procedure for the Preparation of Intermediates Via $S_NAr$ Reaction of a Pyrazole with 4,6-Dichloropyrimidine as Exemplified by the Preparation of Intermediate 10, 4-chloro-6-[($^2H_3$)-1H-pyrazol-1-yl]pyrimidine.

A mixture of 4,6-dichloropyrimidine (Intermediate 2, 1.50 g, 10.1 mmol), pyrazole-$d_4$ (Intermediate 11, 761 mg, 10.6 mmol) and $K_2CO_3$ (1.46 g, 10.6 mmol) in DMF (10 mL) was stirred at rt for 17 h before adding to $H_2O$ (50 mL). After stirring for 5 min the title compound (1.20 g, 6.54 mmol) was isolated by filtration as a pale yellow solid.

Data in table 1.

Intermediate 12,
4-chloro-6-(4-fluoro-1H-pyrazol-1-yl)pyrimidine

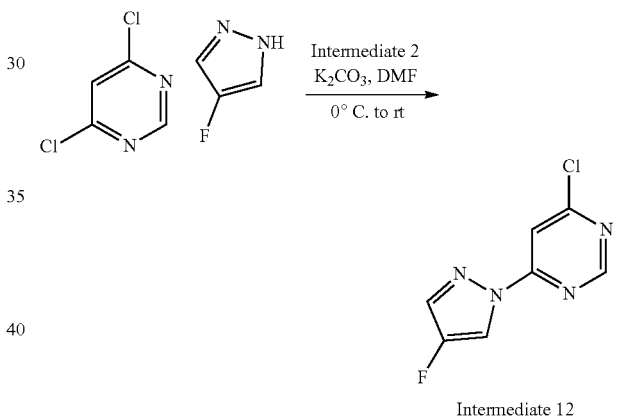

Intermediate 12

The title compound (622 mg, 3.13 mmol) was prepared from 4-fluoropyrazole (Intermediate 13, 551 mg, 6.40 mmol), 4,6-dichloropyrimidine (Intermediate 2, 908 mg, 4.57 mmol) and $K_2CO_3$ (884 mg, 6.40 mmol) in DMF (20 mL) using the methods of Intermediate 10.

Data in table 1.

Routes 4 and 5

Typical Procedure for the Preparation of Intermediates Via Suzuki Coupling of Boronic Acids or Esters with 4,6-Dichloropyrimidine as Exemplified by the Preparation of Intermediate 14, 3-(6-chloropyrimidin-4-yl)-5-fluorobenzonitrile.

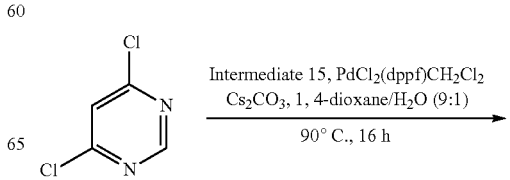

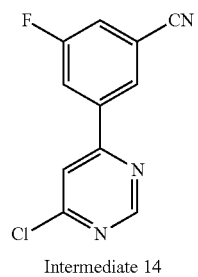

Intermediate 14

4,6-Dichloropyrimidine (Intermediate 2, 1.8 g, 12.2 mmol), 3-cyano-5-fluorophenylboronic acid (Intermediate 15, 2.0 g, 12.1 mmol) and cesium carbonate (7.8 g, 23.9 mmol) were dissolved in 1,4-dioxane/water (9:1, 10 mL) and the mixture was degassed by purging with $N_2$ for 5 min. [1,1'-Bis(diphenylphosphino)ferrocene]dichloropalladium (II), complex with dichloromethane (490 mg, 0.60 mmol) was added and the reaction mixture was stirred at 90° C. for 16 h. The reaction mixture was partitioned between $H_2O$ (250 mL) and EtOAc (150 mL), the phases were separated and the aqueous phase extracted with EtOAc (2×150 mL). The combined organic phases were dried ($Na_2SO_4$) and concentrated in vacuo. Purification by gradient flash chromatography, eluting with 0-10% EtOAc in hexane yielded the title compound (1.0 g, 4.28 mmol) as a white solid.

Data in table 1.

Intermediate 16, 3-chloro-5-(6-chloropyrimidin-4-yl)-4-fluorobenzonitrile

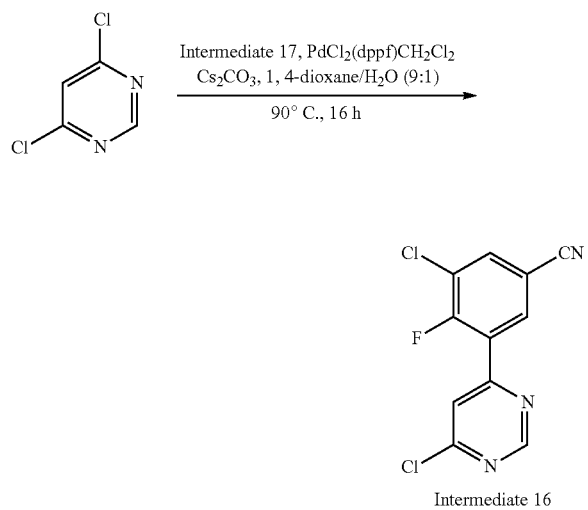

Intermediate 16

The title compound (110 mg, 0.41 mmol) was prepared from 3-chloro-5-cyano-2-fluorophenylboronic acid, pinacol ester (Intermediate 17, 245 mg, 0.87 mmol) and 4,6-dichloropyrimidine (Intermediate 2, 200 mg, 1.34 mmol) using the methods of Intermediate 14.

Data in table 1.

Intermediate 18, 3-chloro-5-(6-chloropyrimidin-4-yl)benzonitrile

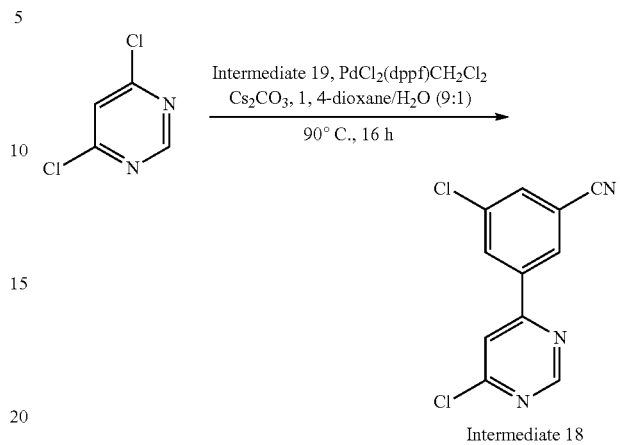

Intermediate 18

The title compound (4.0 g, 16.0 mmol) was prepared from 3-chloro-5-(4,4,5,5-tetramethyl-1,3,2-dioxaborolan-2-yl)benzonitrile (Intermediate 19, 17.6 g, 66.8 mmol) and 4,6-dichloropyrimidine (Intermediate 2, 9.0 g, 60.4 mmol) using the methods of Intermediate 14.

Data in table 1.

Preparation of intermediate 19, 3-chloro-5-(4,4,5,5-tetramethyl-1,3,2-dioxaborolan-2-yl)benzonitrile

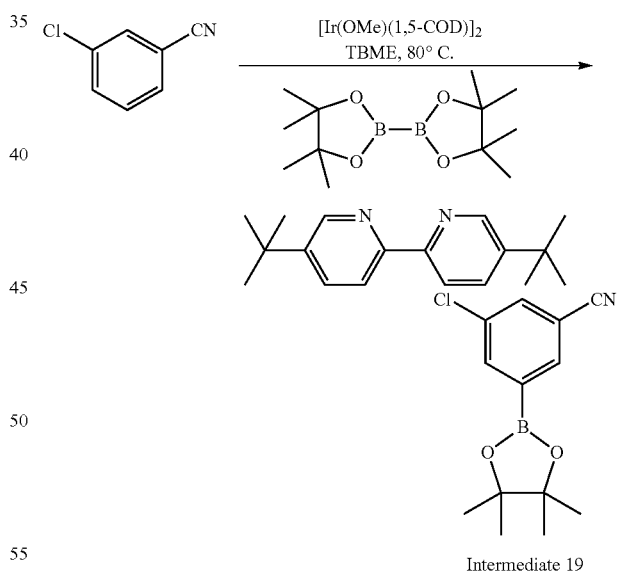

Intermediate 19

The title compound was prepared from 3-chlorobenzonitrile (Intermediate 20, 1.23 g, 8.94 mmol), (1,5-cyclooctadiene)(methoxy)iridium(I) dimer (89 mg, 0.13 mmol), 4,4'-di-tert-butyl-2,2'-dipyridyl (72 mg, 0.27 mmol) and bis(pinacolato)diboron (2.49 g, 9.81 mmol) in TBME (24 mL) using the methods of Intermediate 28, step 2. Purification by gradient flash chromatography, eluting with 0-10% diethyl ether in isohexane yielded the title compound (1.39 g, 5.27 mmol) as a clear oil.

Data in table 1.

Intermediate 21, 3-(6-chloropyrimidin-4-yl)-5-methylbenzonitrile

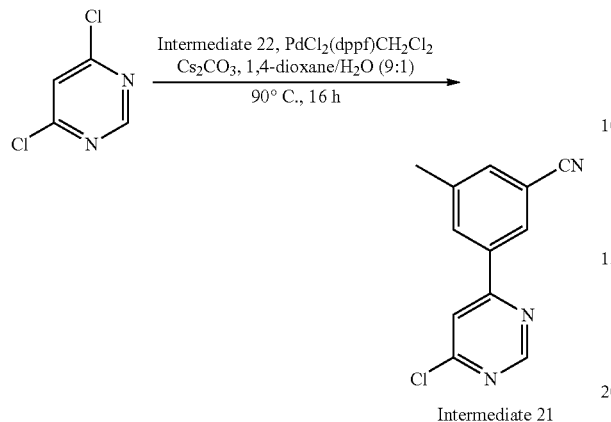

Intermediate 21

The title compound (170 mg, 0.74 mmol) was prepared from 3-methyl-5-(4,4,5,5-tetramethyl-1,3,2-dioxaborolan-2-yl)benzonitrile (Intermediate 22, 326 mg, 1.34 mmol) and 4,6-dichloropyrimidine (Intermediate 2, 200 mg, 1.34 mmol) using the methods of Intermediate 14.

Data in table 1.

Preparation of intermediate 22, 3-methyl-5-(4,4,5,5-tetramethyl-1,3,2-dioxaborolan-2-yl)benzonitrile

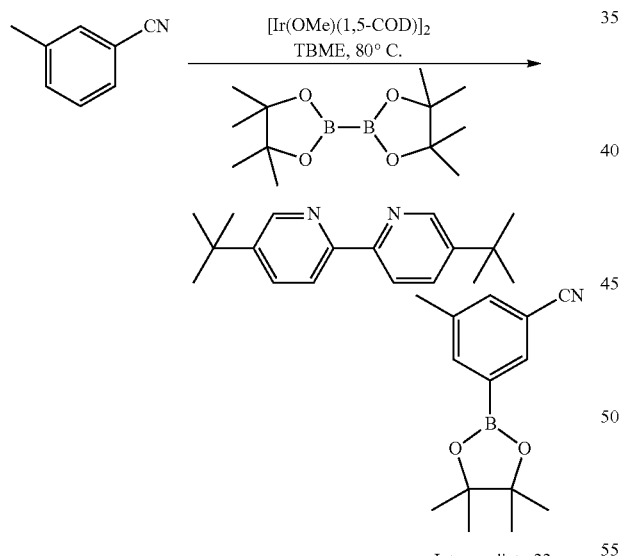

Intermediate 22

The title compound was prepared from 3-methylbenzonitrile (Intermediate 23, 1.76 mL, 15.0 mmol), (1,5-cyclooctadiene)(methoxy)iridium(I) dimer (149 mg, 0.23 mmol), 4,4'-di-tert-butyl-2,2'-dipyridyl (121 mg, 0.45 mmol) and bis(pinacolato)diboron (4.19 g, 16.5 mmol) in TBME (30 mL) using the methods of Intermediate 28, step 2. Purification by gradient flash chromatography, eluting with 0-10% diethyl ether in isohexane yielded the title compound (2.34 g, 9.63 mmol) as a white solid.

Data in table 1.

Preparation of intermediate 38, 3-(methoxymethyl)-5-(4,4,5,5-tetramethyl-1,3,2-dioxaborolan-2-yl)benzonitrile

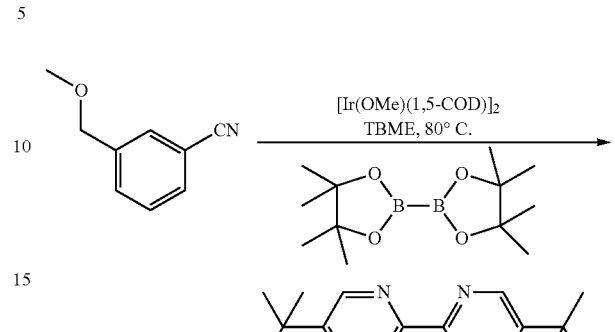

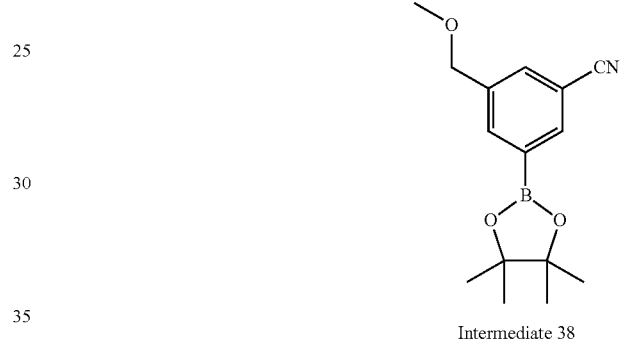

Intermediate 38

The title compound was prepared from 3-(methoxymethyl)benzonitrile (Intermediate 37, 221 mg, 15.0 mmol), (1,5-cyclooctadiene)(methoxy)iridium(I) dimer (14 mg, 0.02 mmol), 4,4'-di-tert-butyl-2,2'-dipyridyl (12 mg, 0.05 mmol) and bis(pinacolato)diboron (419 mg, 1.65 mmol) in TBME (5 mL) at 80° C. for 1 h using microwave irradiation using the methods of Intermediate 28, step 2. Purification by gradient flash chromatography, eluting with 0-8% ethyl acetate in hexane yielded the title compound (285 mg, 1.04 mmol) as a white solid.

Data in table 1.

Intermediate 39, 3-(6-chloropyrimidin-4-yl)-5-(methoxymethyl)benzonitrile

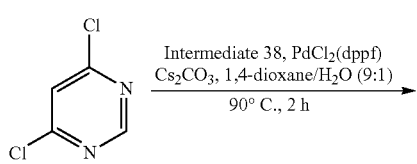

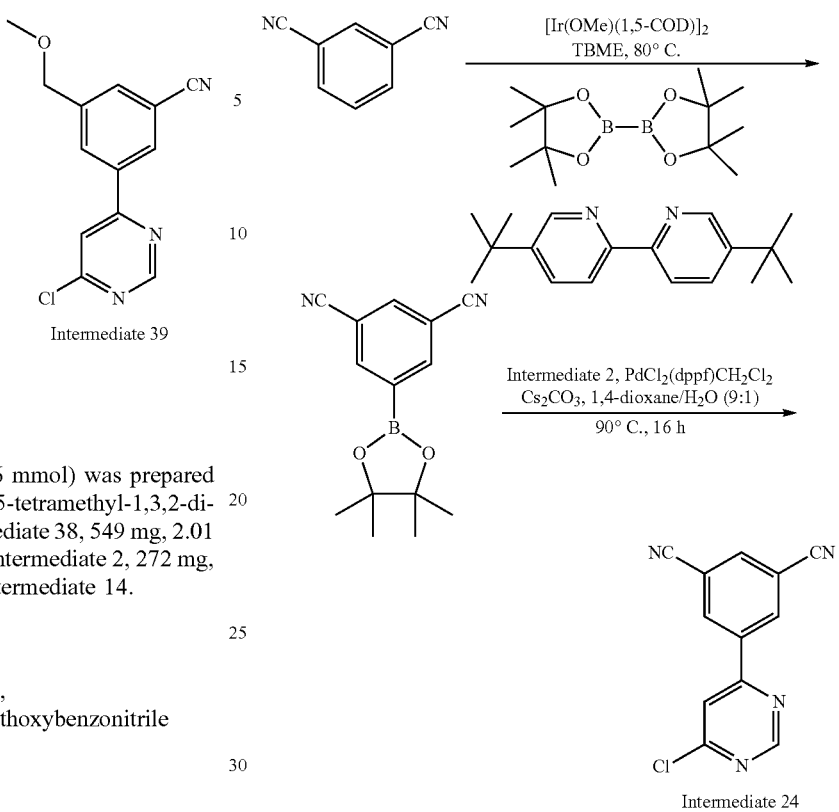

The title compound (300 mg, 1.16 mmol) was prepared from 3-(methoxymethyl)-5-(4,4,5,5-tetramethyl-1,3,2-dioxaborolan-2-yl)benzonitrile (Intermediate 38, 549 mg, 2.01 mmol) and 4,6-dichloropyrimidine (Intermediate 2, 272 mg, 1.83 mmol) using the methods of Intermediate 14.

Data in table 1.

Intermediate 41,
3-(6-chloropyrimidin-4-yl)-5-methoxybenzonitrile

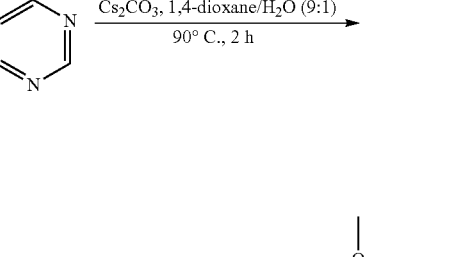

The title compound (3.2 g, 13.2 mmol) was prepared from 3-methoxy-5-(4,4,5,5-tetramethyl-1,3,2-dioxaborolan-2-yl)benzonitrile (Intermediate 40, 5.1 g, 19.7 mmol) and 4,6-dichloropyrimidine (Intermediate 2, 2.7 g, 18.1 mmol) using the methods of Intermediate 14.

Data in table 1.

Typical Procedure for the Preparation of Intermediates Via Ir-Catalysed Boronic Ester Formation and Subsequent Suzuki Coupling with 4,6-Dichloropyrimidine as Exemplified by the Preparation of Intermediate 24, 5-(6-Chloropyrimidin-4-yl)benzene-1,3-dicarbonitrile.

Under $N_2$, a solution of (1,5-cyclooctadiene)(methoxy) iridium(I) dimer (505 mg, 0.76 mmol), 4,4'-di-tert-butyl-2,2'-dipyridyl (409 mg, 1.52 mmol) and bis(pinacolato)diboron (13.4 g, 52.7 mmol) in TBME (135 mL) was prepared. A portion of this solution (15 mL) was added to isophthalonitrile (Intermediate 25, 700 mg, 5.46 mmol) and the mixture heated for 1 h at 80° C. in a microwave reactor. The reaction was repeated 8 more times on this scale and the combined reaction mixtures were concentrated in vacuo. Purification by gradient flash chromatography, eluting with 0-10% EtOAc in hexane yielded 5-(4,4,5,5-tetramethyl-1,3,2-dioxaborolan-2-yl)isophthalonitrile (5.6 g, 22.0 mmol).

TLC: Rf 0.3, Hexane/Ethyl acetate 4:1

$^1$H NMR: (400 MHz, DMSO-$d_6$) δ: 1.33 (s, 12H), 8.25-8.27 (m, 2H), 8.60-8.61 (m, 1H)

4,6-Dichloropyrimidine (Intermediate 2, 3.28 g, 22.0 mol), 5-(4,4,5,5-tetramethyl-1,3,2-dioxaborolan-2-yl) isophthalonitrile (5.6 g, 22.0 mmol) and cesium carbonate (14.4 g, 44.2 mmol) were dissolved in 1,4-dioxane/water (9:1, 60 mL) and the mixture was degassed by purging with $N_2$ for 10 min. [1,1'-Bis(diphenylphosphino)ferrocene]dichloropalladium(II) (806 mg, 1.10 mmol) was added and the reaction mixture was stirred at 90° C. for 3 h. After cooling to rt the reaction mixture was partitioned between $H_2O$ (250 mL) and EtOAc (150 mL), the phases were separated and the aqueous phase was extracted with EtOAc (2×150 mL). The combined organic phases were dried ($Na_2SO_4$) and concentrated in vacuo. Purification by gradient flash chromatography, eluting with 0-15% EtOAc in hexane yielded the title compound (1.70 g, 7.06 mmol) as a white solid.

Data in table 1.

Preparation of Further Boronic Acid and Boronic Ester Intermediates

Preparation of Intermediate 26, (3-Cyano-5-Methylphenyl)Boronic Acid

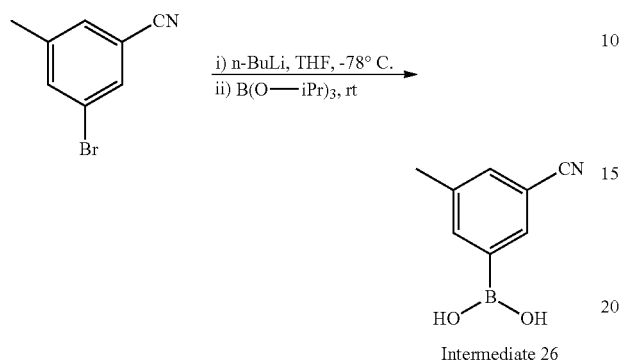

Intermediate 26

3-Bromo-5-methylbenzonitrile (Intermediate 27, 250 mg, 1.28 mmol) was dissolved in THF (5 mL), cooled to −78° C. and n-BuLi (1.19 mL of a 1.6 M solution in THF, 1.91 mmol) was added dropwise. After stirring at −78° C. for 30 min triisopropyl borate (0.64 mL, 2.81 mmol) was added dropwise at −78° C., the cooling bath was removed and the reaction mixture was stirred at rt for 16 h. Saturated aqueous ammonium chloride solution (50 mL) and EtOAc (25 mL) were added and the phases were separated. The aqueous phase was extracted with EtOAc (2×25 mL), the combined organic phases were dried (Na$_2$SO$_4$) and concentrated in vacuo to yield the crude title compound (200 mg) as an off-white solid which was used without further purification. Data in table 1.

Preparation of Intermediate 28, 3-(fluoromethyl)-5-(4,4,5,5-tetramethyl-1,3,2-dioxaborolan-2-yl)benzonitrile

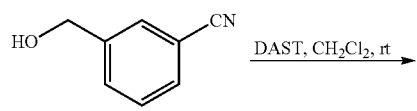

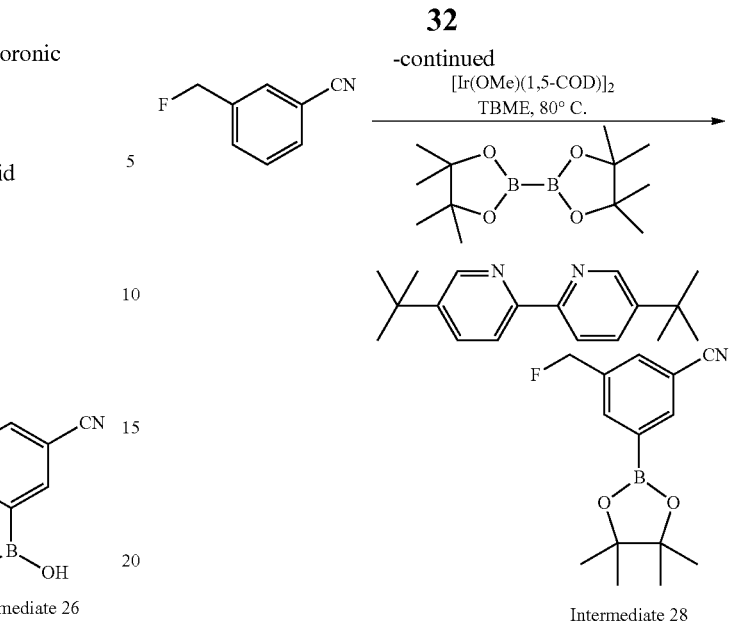

Intermediate 28

(Diethylamino)sulfur trifluoride (2.01 mL, 2.0 mmol) was added to a solution of 3-(hydroxymethyl)benzonitrile (Intermediate 29, 1.0 g, 7.50 mmol) in CH$_2$Cl$_2$ (50 mL) and the resulting mixture was stirred at rt for 2 h. Saturated aqueous NaHCO$_3$ solution (30 mL) and CH$_2$Cl$_2$ (20 mL) were added and the phases were separated. The aqueous phase was extracted with CH$_2$Cl$_2$ (2×25 mL) and the combined organic phases were dried (Na$_2$SO$_4$) and concentrated in vacuo. Purification by gradient flash chromatography, eluting with 0-25% EtOAc in hexane yielded 3-(fluoromethyl)benzonitrile (500 mg, 3.70 mmol).

$^1$H NMR: (400 MHz, CDCl$_3$) δ: 5.45 (d, J=47, 2H), 7.53-7.57 (m, 1H), 7.62-7.70 (m, 3H)

A mixture of 3-(fluoromethyl)benzonitrile (500 mg, 3.70 mmol), (1,5-cyclooctadiene) (methoxy)iridium(I) dimer (74 mg, 0.11 mmol), 4,4'-di-tert-butyl-2,2'-dipyridyl (60 mg, 0.22 mmol) and bis(pinacolato)diboron (1.1 g, 4.06 mmol) were dissolved in TBME (15 mL). The reaction mixture was heated at 80° C. for 16 h under N$_2$ before cooling to rt and partitioning between H$_2$O (50 mL) and EtOAc (25 mL). The aqueous phase was extracted with EtOAc (2×25 mL), the combined organic phases were dried (Na$_2$SO$_4$) and concentrated in vacuo. Purification by gradient flash chromatography, eluting with 0-80% EtOAc in hexane yielded crude 3-(fluoromethyl)-5-(4,4,5,5-tetramethyl-1,3,2-dioxaborolan-2-yl)benzonitrile (Intermediate 28, 950 mg) which was used in the subsequent step without characterisation or further purification.

TABLE 1

| Intermediate | Name | Data |
| --- | --- | --- |
| 1 | 4-chloro-6-(pyridin-2-yl)pyrimidine | LCMS: m/z 192.2 (M + H)+ (ES+), at 2.94 min, 98% $^1$H NMR: (400 MHz, DMSO-d$_6$) δ: 7.65 (ddd, J = 7.6, 4.8, 1.1, 1H), 8.08 (td, J = 7.8, 1.8, 1H), 8.41-8.49 (m, 2H), 8.79-8.85 (m, 1H), 9.19 (d, J = 1.2, 1 H) |
| 2 | 4,6-dichloropyrimidine | Commercially available, CAS 1193-21-1 |
| 3 | 2-(tributylstannyl)pyridine | Commercially available, CAS 17997-47-6 |

TABLE 1-continued

| Intermediate | Name | Data |
|---|---|---|
| 4 | 6-(6-chloropyrimidin-4-yl)pyridine-3-carbonitrile | $^1$H NMR: (400 MHz, DMSO-$d_6$) δ: 8.47 (d, J = 1.2, 1H), 8.60 (d, J = 1.5, 2H), 9.25-9.29 (m, 2H) |
| 5 | 2-bromo-5-cyanopyridine | Commercially available, CAS 139585-70-9 |
| 6 | 3-(6-chloropyrimidin-4-yl)pyridazine | TLC: Rf 0.3, Hexane/Ethyl acetate 4:1 |
| 7 | 3-bromopyridazine | Commercially available, CAS 88491-61-6 |
| 8 | 6-chloro-4,4'-bipyrimidine | $^1$H NMR: (400 MHz, DMSO-$d_6$) δ: 8.43 (dd, J = 5.2, 1.2, 1H), 8.49 (d, J = 1.2, 1H), 9.13 (d, J = 4.9, 1H), 9.29 (d, J = 0.9, 1H), 9.45 (d, J = 1.2, 1H) |
| 9 | 4-pyrimidinecarboxylic acid | Commercially available, CAS 31462-59-6 |
| 10 | 4-chloro-6-[($^2$H$_3$)-1H-pyrazol-1-yl]pyrimidine | $^1$H NMR: (400 MHz, CDCl$_3$) δ: 7.96 (s, 1H), 8.78 (s, 1H) |
| 11 | pyrazole-d$_4$ | Commercially available, CAS 53013-62-0 |
| 12 | 4-chloro-6-(4-fluoro-1H-pyrazol-1-yl)pyrimidine | $^1$H NMR: (400 MHz, CDCl$_3$) δ: 7.70 (d, J = 3.9, 1H), 7.94 (d, J = 0.8, 1H), 8.40 (d, J = 3.9, 1H), 8.79 (s, 1H) |
| 13 | 4-fluoropyrazole | Commercially available, CAS 35277-02-2 |
| 14 | 3-(6-chloropyrimidin-4-yl)-5-fluorobenzonitrile | LCMS: m/z not observed (ES+), at 3.89 min, 95% $^1$H NMR: (400 MHz, DMSO-$d_6$) δ: 8.12-8.18 (m, 1H), 8.42-8.47 (m, 1H), 8.55 (d, J = 0.9, 1H), 8.61 (t, J = 1.4, 1H), 9.19 (d, J = 1.2, 1H) |
| 15 | 3-cyano-5-fluorophenylboronic acid | Commercially available, CAS 304858-67-1 |
| 16 | 3-chloro-5-(6-chloropyrimidin-4-yl)-4-fluorobenzonitrile | $^1$H NMR: (400 MHz, DMSO-$d_6$) δ: 8.21 (s, 1H), 8.43-8.48 (m, 1H), 8.51-8.58 (m, 1H), 9.26 (d, J = 1.2, 1H) |
| 17 | 3-chloro-5-cyano-2-fluorophenylboronic acid, pinacol ester | Commercially available, CAS 1218790-15-8 |
| 18 | 3-chloro-5-(6-chloropyrimidin-4-yl)benzonitrile | LCMS: m/z not observed (ES+), at 3.91 min, 95% $^1$H NMR: (400 MHz, DMSO-$d_6$) δ: 8.27 (s, 1H), 8.53 (s, 1H), 8.59 (s, 1H), 8.66 (s, 1H), 9.16 (s, 1H) |
| 19 | 3-chloro-5-(4,4,5,5-tetramethyl-1,3,2-dioxaborolan-2-yl)benzonitrile | $^1$H NMR: (400 MHz, CDCl$_3$) δ: 1.35 (s, 12H), 7.69-7.70 (m, 1H), 7.96-7.98 (m, 2H) |
| 20 | 3-chlorobenzonitrile | Commercially available, CAS 766-84-7 |
| 21 | 3-(6-chloropyrimidin-4-yl)-5-methylbenzonitrile | $^1$H NMR: (400 MHz, DMSO-$d_6$) δ: 2.47 (s, 3H), 7.91-7.94 (m, 1H), 8.43-8.54 (m, 3H), 9.16 (d, J = 0.9, 1H) |
| 22 | 3-methyl-5-(4,4,5,5-tetramethyl-1,3,2-dioxaborolan-2-yl)benzonitrile | $^1$H NMR: (400 MHz, CDCl$_3$) δ: 1.35 (s, 12H), 2.38 (s, 3H), 7.52 (s, 1H), 7.82 (s, 1H), 7.89 (s, 1H) |
| 23 | 3-methylbenzonitrile | Commercially available, CAS 620-22-4 |
| 24 | 5-(6-chloropyrimidin-4-yl)benzene-1,3-dicarbonitrile | $^1$H NMR: (400 MHz, DMSO-$d_6$) δ: 8.60 (d, J = 1.2, 1H), 8.70-8.74 (m, 1H), 9.00 (d, J = 1.5, 2H), 9.22 (d, J = 0.9, 1H) |
| 25 | isophthalonitrile | Commercially available, CAS 626-17-5 |
| 26 | (3-cyano-5-methylphenyl)boronic acid | TLC: Rf 0.3, Hexane/Ethyl acetate 1:1 |
| 27 | 3-bromo-5-methylbenzonitrile | Commercially available, CAS 124289-21-0 |

TABLE 1-continued

| Intermediate | Name | Data |
|---|---|---|
| 28 | 3-(fluoromethyl)-5-(4,4,5,5-tetramethyl-1,3,2-dioxaborolan-2-yl)benzonitrile | — |
| 29 | 3-(hydroxymethyl)benzonitrile | Commercially available, CAS 874-97-5 |
| 30 | 2-bromo-5-fluoropyridine | Commercially available, CAS 41404-58-4 |
| 31 | 5-methyl-2-(tributylstannyl)pyridine | Commercially available, CAS 189195-41-3 |
| 32 | 5-chloro-2-(tributylstannyl)pyridine | Commercially available, CAS 611168-63-9 |
| 33 | 5-methyl-2-(tributylstannyl)pyridine | Commercially available, CAS 189195-41-3 |
| 34 | 4-chloro-6-(1H-pyrazol-1-yl)pyrimidine | Commercially available, CAS 114833-95-3 |
| 35 | 2-chloro-4-(1H-pyrazol-1-yl)pyridine | Commercially available, CAS 1209459-70-0 |
| 36 | 4-bromo-2-(1H-pyrazol-1-yl)pyridine | Commercially available, CAS 1159814-68-2 |
| 37 | 3-(methoxymethyl)benzonitrile | Commercially available, CAS 1515-86-2 |
| 38 | 3-(methoxymethyl)-5-(4,4,5,5-tetramethyl-1,3,2-dioxaborolan-2-yl)benzonitrile. | $^1$H NMR: (400 MHz, DMSO-$d_6$) δ: 1.31 (s, 12H), 3.31 (s, 3H), 4.48 (s, 2H), 7.88-7.94 (m, 3H) |
| 39 | 3-(6-chloropyrimidin-4-yl)-5-(methoxymethyl)benzonitrile | $^1$H NMR: (400 MHz, DMSO-$d_6$) δ: 3.36 (s, 3H), 4.57 (s, 2H), 7.98-8.00 (m, 1H), 8.50-8.55 (m, 2H), 8.63-8.66 (m, 1H), 9.16 (d, J = 0.9, 1H) |
| 40 | 3-methoxy-5-(4,4,5,5-tetramethyl-1,3,2-dioxaborolan-2-yl)benzonitrile | Commercially available, CAS 1035266-33-1 |
| 41 | 3-(6-chloropyrimidin-4-yl)-5-methoxybenzonitrile | $^1$H NMR: (400 MHz, DMSO-$d_6$) δ: 3.92 (s, 3H), 7.68-7.71 (m, 1H), 8.10 (dd, J = 2.4, 1.5, 1H), 8.27-8.30 (m, 1H), 8.52 (d, J = 1.2, 1H), 9.16 (d, J = 1.2, 1H) |

Synthesis of Examples

Route 1

Typical Procedure for the Preparation of Examples Via Suzuki Coupling with a Commercially Available or Synthesized Boronic Acid or Boronic Ester as Exemplified by the Preparation of Example 1, 3-chloro-4-fluoro-5-[6-(pyridin-2-yl)pyrimidin-4-yl]benzonitrile

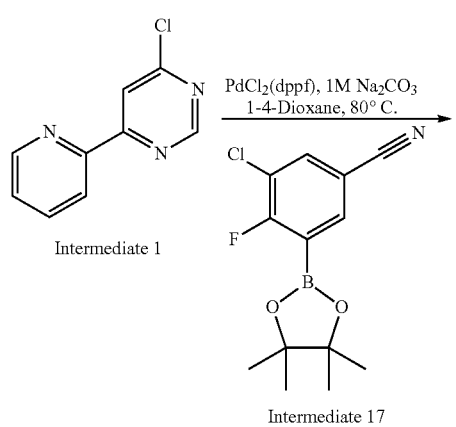

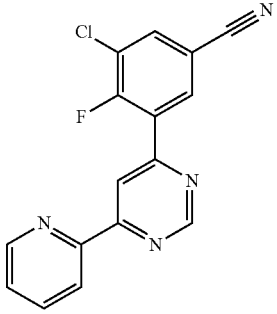

Example 1

A mixture of 4-chloro-6-(pyridin-2-yl)pyrimidine (Intermediate 1, 96 mg, 0.50 mmol), 3-chloro-5-cyano-2-fluorophenylboronic acid, pinacol ester (Intermediate 17, 169 mg, 0.60 mmol), [1,1'-bis(diphenylphosphino)ferrocene]dichloropalladium(II) (22 mg, 0.03 mmol) and 1 M aqueous $Na_2CO_3$ solution (1.25 mL, 1.25 mmol) in 1,4-dioxane (1.2 mL) was degassed by purging with $N_2$ for 5 min before heating at 80° C. for 2 h. After cooling to rt and concentration in vacuo $CH_2Cl_2$ and $H_2O$ were added and the phases were separated. The aqueous phase was extracted with $CH_2Cl_2$ and the combined organic phases were concentrated in vacuo. Purification by gradient flash chromatography, eluting with 10-30% EtOAc in isohexane followed by trituration with diethyl ether yielded the title compound (35 mg, 0.11 mmol) as a white solid.

Data in table 2.

Typical Procedure for the Preparation of Examples Via Ir-Catalysed Synthesis of a Boronic Ester Followed by Suzuki Coupling as Exemplified by the Preparation of Example 2, 3-chloro-5-[6-(pyridin-2-yl)pyrimidin-4-yl]benzonitrile.

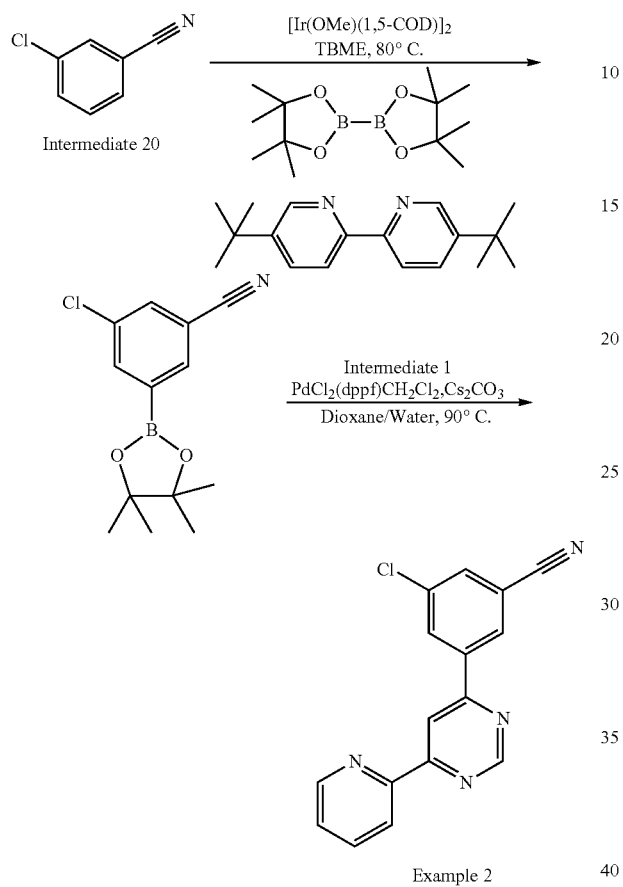

Example 2

A mixture of 3-chlorobenzonitrile (Intermediate 20, 1.0 g, 7.3 mmol), (1,5-cyclooctadiene)(methoxy)iridium(I) dimer (144 mg, 0.22 mmol), 4,4'-di-tert-butyl-2,2'-dipyridyl (117 mg, 0.44 mmol) and bis(pinacolato)diboron (2.0 g, 7.88 mmol) were dissolved in TBME (15 mL). The reaction mixture was heated at 80° C. for 16 h under $N_2$ before cooling to rt and partitioning between $H_2O$ (50 mL) and EtOAc (25 mL). The aqueous phase was extracted with EtOAc (2×25 mL), the combined organic phases were dried ($Na_2SO_4$) and concentrated in vacuo. Purification by gradient flash chromatography, eluting with 0-80% EtOAc in hexane yielded crude 3-chloro-5-(4,4,5,5-tetramethyl-1,3,2-dioxaborolan-2-yl)benzonitrile (1.90 g) which was used in the subsequent step without characterisation or further purification.

A mixture of 4-chloro-6-(pyridin-2-yl)pyrimidine (Intermediate 1) (200 mg, 1.04 mmol), crude 3-chloro-5-(4,4,5,5-tetramethyl-1,3,2-dioxaborolan-2-yl)benzonitrile (275 mg) and cesium carbonate (678 mg, 2.08 mmol) were dissolved in dioxane/water (9:1, 10 mL) and the mixture was degassed by purging with $N_2$ for 5 min. [1,1'-Bis(diphenylphosphino)ferrocene]dichloropalladium(II), complex with dichloromethane (42.6 mg, 0.05 mmol) was added and the reaction mixture was stirred at 90° C. for 16 h. After cooling to rt the reaction mixture was partitioned between $H_2O$ (50 mL) and EtOAc (25 mL), the aqueous phase was extracted with EtOAc (2×25 mL) and the combined organic phases dried ($Na_2SO_4$). After concentration in vacuo purification by gradient flash chromatography, eluting with 0-30% EtOAc in hexane yielded the title compound (45 mg, 0.15 mmol) as a light yellow solid.

Data in table 2.

Route 2

Example 6, 3-(4,4'-bipyrimidin-6-yl)-5-chlorobenzonitrile

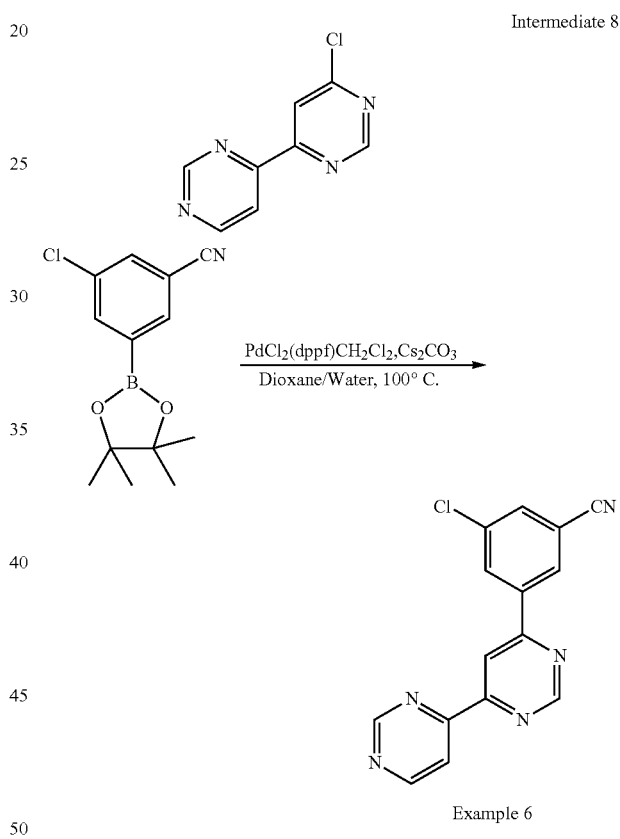

Example 6

The title compound (27 mg, 0.09 mmol) was prepared from 6-chloro-4,4'-bipyrimidine (Intermediate 8, 40 mg, 0.21 mmol) and crude 3-chloro-5-(4,4,5,5-tetramethyl-1,3,2-dioxaborolan-2-yl)benzonitrile (50 mg) at 100° C. using the methods of Example 2, 3-chloro-5-[6-(pyridin-2-yl)pyrimidin-4-yl]benzonitrile.

Data in table 2.

Route 3

Typical Procedure for the Preparation of Examples Via Suzuki Coupling with a Commercially Available or Synthesized Boronic Acid or Boronic Ester as Exemplified by the Preparation of Example 7, 3-methyl-5-[6-(1H-pyrazol-1-yl)pyrimidin-4-yl]benzonitrile

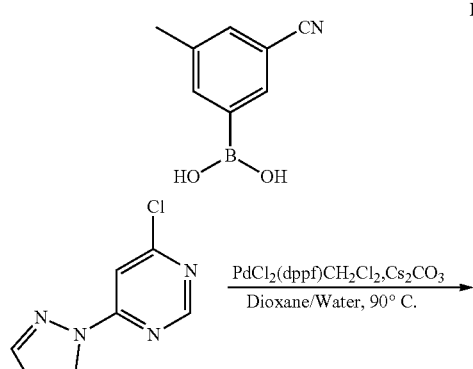

Intermediate 26

Intermediate 24

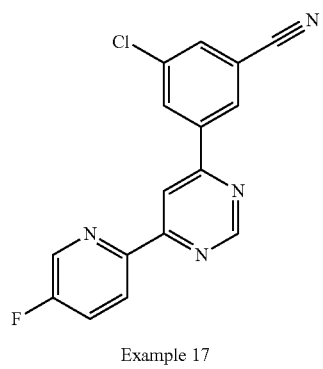

Example 17

A mixture of 2-bromo-5-fluoropyridine (Intermediate 30, 500 mg, 2.89 mmol) and hexamethylditin (946 mg, 2.89 mmol) in DME (10 mL) was degassed by purging with $N_2$ for 5 min before the addition of tetrakis(triphenylphosphine)palladium(0) (166 mg, 0.14 mmol). The reaction mixture was stirred at 110° C. for 16 h before cooling to rt and partitioning between $H_2O$ (50 mL) and EtOAc (25 mL). The phases were separated and the aqueous phase was extracted with EtOAc (2×25 mL). The combined organic phases were dried ($Na_2SO_4$) and concentrated in vacuo to yield crude 5-fluoro-2-(trimethylstannyl)pyridine (700 mg) which was used in the subsequent step without characterisation or further purification.

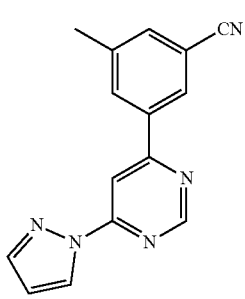

Example 7

The title compound (27 mg, 0.10 mmol) was prepared from 4-chloro-6-(1H-pyrazol-1-yl)pyrimidine (Intermediate 34, 225 mg, 1.25 mmol) and (3-cyano-5-methylphenyl)boronic acid (Intermediate 26, 200 mg, 1.24 mmol) at 90° C. using the methods of Example 2, 3-chloro-5-[6-(pyridin-2-yl)pyrimidin-4-yl]benzonitrile.

Data in table 2.

Route 4

Typical Procedure for the Preparation of Examples Via Synthesis of a Trialkylstannane where not Commercially Available, Followed by Stille Coupling as Exemplified by the Preparation of Example 17, 3-chloro-5-[6-(5-fluoropyridin-2-yl)pyrimidin-4-yl]benzonitrile.

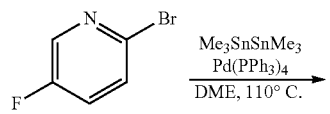

Intermediate 30

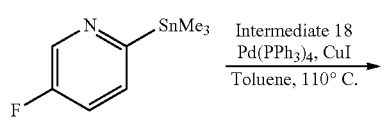

3-chloro-5-(6-chloropyrimidin-4-yl)benzonitrile (Intermediate 18, 100 mg, 0.39 mmol) and crude 5-fluoro-2-(trimethylstannyl)pyridine (114 mg) were dissolved in toluene (15 mL) and the reaction mixture was degassed by purging with $N_2$ for 5 min before the addition of tetrakis(triphenylphosphine)palladium(0) (46.2 mg, 0.04 mmol) and copper(I) iodide (7.6 mg, 0.03 mmol). The reaction mixture was stirred at 110° C. for 16 h before cooling to rt and partitioning between $H_2O$ (50 mL) and EtOAc (25 mL). The phases were separated and the aqueous phase was extracted with EtOAc (2×25 mL). The combined organic phases were dried ($Na_2SO_4$) and concentrated in vacuo. Purification by gradient flash chromatography, eluting with 0-10% EtOAc in hexane yielded the title compound (37 mg, 0.12 mmol) as a pale yellow solid.

Data in table 2.

Route 5

Typical Procedure for the Preparation of Examples Via Negishi Coupling as Exemplified by the Preparation of Example 17, 3-chloro-5-[6-(5-fluoropyridin-2-yl)pyrimidin-4-yl]benzonitrile.

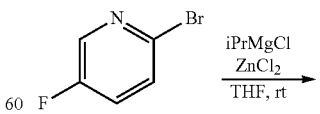

Intermediate 30

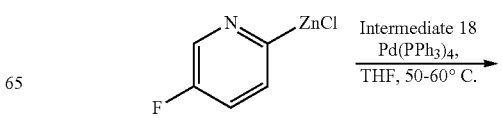

-continued

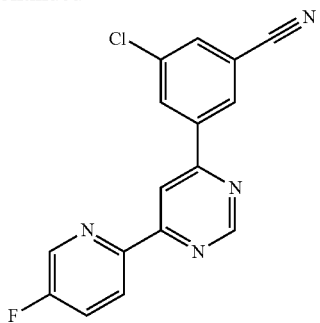

Example 17

To a dried flask under nitrogen was added i-PrMgCl (2M in THF, 11.2 mL, 22.4 mmol) and 2-bromo-5-fluoropyridine (Intermediate 30, 3.94 g, 22.4 mmol) in THF (40 mL). After stirring at rt for 3.5 h ZnCl₂ (0.5 M in THF, 51.2 mL, 25.6 mmol) was added dropwise maintaining the temperature below 25° C. and the mixture was stirred for a further 1 h. Separately, under nitrogen to a solution of 3-chloro-5-(6-chloropyrimidin-4-yl)benzonitrile (Intermediate 18, 4.00 g, 16.0 mmol) in THF (80 mL) was added tetrakis(triphenylphosphine)palladium (924 mg, 0.80 mmol) and the previously prepared zincate solution was then added dropwise and the mixture was heated to 50-60° C. for 18 h. After cooling to rt the mixture was evaporated to approximately 10% of its original volume, diluted with EtOAc (400 mL) and washed with water (500 mL). The aqueous phase was then extracted with EtOAc (3×400 mL) and the combined organic phases were washed with brine (500 mL), dried (anhydrous Na₂SO₄), filtered and concentrated in vacuo. Purification by flash chromatography, eluting with 5% EtOAc in hexane yielded the title compound (2.97 g, 9.56 mmol) as a white solid. The purified compound was combined with product batches from other reactions (17.6 g total material) and re-crystallised from hot EtOAc to yield the title compound (12.5 g, 40.2 mmol) as a white solid.

Data in table 2.

TABLE 2

| Ex No. | Name | Intermediates | Synthetic route | ¹H NMR | LCMS data |
|---|---|---|---|---|---|
| 1 | 3-chloro-4-fluoro-5-[6-(pyridin-2-yl)pyrimidin-4-yl]benzonitrile | 1, 17 | 1 | (400 MHz, CDCl₃) δ: ppm 7.43-7.54 (m, 1H) 7.84-7.94 (m, 2H) 8.47 (dd, J = 6.1, 2.1, 1H) 8.56 (d, J = 7.8, 1H) 8.76 (d, J = 3.9, 1H) 8.93 (d, J = 0.8, 1H) 9.40 (d, J = 1.2, 1H) | m/z not observed (ES⁺), at 4.32 min, 100% |
| 2 | 3-chloro-5-[6-(pyridin-2-yl)pyrimidin-4-yl]benzonitrile | 1, 20 | 1 | (400 MHz, DMSO-d₆) δ: 7.66 (ddd, J = 7.6, 4.8, 1.2, 1H), 8.09 (td, J = 7.8, 1.8, 1H), 8.30 (dd, J = 2.0, 1.4, 1H), 8.52 (dt, J = 7.9, 0.9, 1H), 8.61-8.72 (m, 1H), 8.77 (t, J = 1.5, 1H), 8.80-8.89 (m, 1H), 9.01 (d, J = 1.2, 1H), 9.45 (d, J = 1.5, 1H) | m/z not observed (ES⁺), at 4.33 min, 100% |
| 3 | 6-[6-(3-chloro-5-cyanophenyl)pyrimidin-4-yl]pyridine-3-carbonitrile | 4, 20 | 1 | (400 MHz, CDCl₃) δ: 7.83-7.86 (m, 1H) 8.22 (dd, J = 8.2, 2.1 Hz, 1H) 8.46-8.53 (m, 2H) 8.76 (d, J = 8.2, 1H) 8.89 (d, J = 1.5, 1H) 9.04-9.09 (m, 1H) 9.44 (d, J = 1.2, 1H) | m/z not observed (ES⁺), at 4.52 min, 100% |
| 4 | 3-methyl-5-[6-(pyridin-2-yl)pyrimidin-4-yl]benzonitrile | 1, 26 | 1 | (400 MHz, CDCl₃) δ: ppm 2.55 (s, 3H), 7.50 (dd, J = 6.4, 4.9, 1H), 7.64 (d, J = 0.6, 1H), 7.93-7.98 (m, 1H), 8.31 (s, 1H), 8.38 (s, 1H), 8.59 (d, J = 7.6, 1H), 8.81 (d, J = 4.0, 1H), 8.87 (d, J = 0.9, 1H), 9.38 (d, J = 1.2, 1H) | m/z 273.1 (M + H)⁺ (ES⁺), at 4.03 min, 100% |
| 5 | 3-chloro-5-[6-(pyridazin-3-yl)pyrimidin-4-yl]benzonitrile | 6, 20 | 1 | (400 MHz, CDCl₃) δ: ppm 7.75-7.84 (m, 2H), 8.51-8.53 (m, 2H), 8.70-8.74 (m, 1H), 9.16 (d, J = 1.2, 1H), 9.37-9.40 (m, 1H), 9.45 (d, J = 1.5, 1H) | m/z not observed (ES⁺), at 3.42 min, 100% |
| 6 | 3-(4,4'-bipyrimidin-6-yl)-5-chlorobenzonitrile | 8, 20 | 2 | (400 MHz, CDCl₃) δ: ppm 7.82-7.85 (m, 1H), 8.47-8.54 (m, 3H), 8.91 (d, J = 1.2, 1H), 9.05 (d, J = 5.2, 1H), 9.45 (dd, J = 7.2, 1.4, 2H) | m/z not observed (ES⁺), at 3.63 min, 100% |
| 7 | 3-methyl-5-[6-(1H-pyrazol-1-yl)pyrimidin-4-yl]benzonitrile | 26, 34 | 3 | (400 MHz, DMSO-d₆ + D₂O) δ: ppm 2.47 (s, 3H), 6.71 (dd, J = 2.7, 1.5, 1H), 7.86 (s, 1H), 8.00 (d, J = 1.2, 1H), 8.39 (s, 1H), 8.42-8.50 (m, 2H) 8.75 (d, J = 2.4, 1H), 9.15 (d, J = 0.9, 1H) | m/z 262.2 (M + H)⁺ (ES⁺), at 4.01 min, 100% |
| 8 | 3-chloro-5-[6-(1H-pyrazol-1-yl)pyrimidin-4-yl]benzonitrile | 20, 34 | 3 | (400 MHz, DMSO-d₆) δ: ppm 6.74 (dd, J = 2.7, 1.5, 1H), 8.04-8.06 (m, 1H), 8.30 (dd, J = 2.0, 1.4, 1H), 8.60-8.67 (m, 2H), 8.76-8.80 (m, 2H), 9.21 (d, J = 1.2, 1H) | m/z not observed (ES⁺), at 4.27 min, 100% |
| 9 | 3-chloro-4-fluoro-5-[6-(1H-pyrazol-1-yl)pyrimidin-4-yl]benzonitrile | 17, 34 | 3 | (400 MHz, DMSO-d₆) δ ppm 6.71 (s, 1H), 8.00 (s, 1H), 8.36 (s, 1H), 8.48 (s, 1H), 8.49 (s, 1H), 8.74-8.79 (m, 1H), 9.23 (s, 1H) | m/z not observed (ES⁺), at 4.21 min, 100% |
| 10 | 3-chloro-4-fluoro-5-[4-(1H-pyrazol-1-yl)pyridin-2-yl]benzonitrile | 17, 35 | 3 | (400 MHz, DMSO-d₆) δ ppm 6.68 (s, 1H), 7.90 (s, 1H), 7.98 (d, J = 3.5, 1H), 8.32 (s, 1H), 8.38 (dd, J = 10.2, 6.2, 2H), 8.76-8.83 (m, 2H) | m/z 299.1, 301.0 (M + H)⁺ (ES⁺), at 3.93 min, 100% |
| 11 | 3-chloro-4-fluoro-5-[2-(1H-pyrazol-1-yl)pyridin-4-yl]benzonitrile | 17, 36 | 3 | (400 MHz, DMSO-d₆) δ ppm 6.68 (s, 1H), 7.90 (s, 1H), 7.94-8.01 (m, 1H), 8.32 (s, 1H), 8.37 (dd, J = 10.2, 6.6, 2H), 8.75-8.83 (m, 2H) | m/z 299.0, 301.1 (M + H)⁺ (ES⁺), at 3.93 min, 100% |
| 12 | 3-chloro-4-fluoro-5-[6-(4-fluoro-1H-pyrazol-1-yl)pyrimidin-4-yl]benzonitrile | 12, 17 | 3 | (400 MHz, CDCl₃) δ: ppm 7.72 (d, J = 4.3, 1H), 7.86 (dd, J = 6.2, 2.0, 1H), 8.43-8.49 (m, 3H), 9.07-9.11 (m, 1H) | m/z not observed (ES⁺), at 4.59 min, 100% |
| 13 | 3-methyl-5-{6-[(²H₃)-1H-pyrazol-1-yl]pyrimidin-4-yl}benzonitrile | 10, 21 | 3 | (400 MHz, CDCl₃) δ: ppm 2.52 (s, 3H), 7.62 (s, 1H), 8.21 (s, 1H), 8.30-8.35 (m, 2H), 9.06-9.09 (m, 1H) | m/z 265.3 (M + H)⁺ (ES⁺), at 3.99 min, 100% |

TABLE 2-continued

| Ex No. | Name | Intermediates | Synthetic route | $^1$H NMR | LCMS data |
|---|---|---|---|---|---|
| 14 | 3-chloro-5-{6-[($^2$H$_3$)-1H-pyrazol-1-yl]pyrimidin-4-yl}benzonitrile | 10, 19 | 3 | (400 MHz, CDCl$_3$) δ: ppm 7.79 (s, 1H), 8.35 (d, J = 0.8, 1H), 8.39-8.43 (m, 2H), 9.07-9.11 (m, 1H) | m/z not observed (ES$^+$), at 4.25 min, 98% |
| 15 | 3-chloro-4-fluoro-5-{6-[($^2$H$_3$)-1H-pyrazol-1-yl]pyrimidin-4-yl}benzonitrile | 10, 17 | 3 | (400 MHz, CDCl$_3$) δ: ppm 7.86 (dd, J = 6.2, 2.0, 1H), 8.34-8.49 (m, 2H), 9.11 (d, J = 1.2, 1H) | m/z not observed (ES$^+$), at 4.18 min, 100% |
| 16 | 3-(fluoromethyl)-5-[6-(1H-pyrazol-1-yl)pyrimidin-4-yl]benzonitrile | 28, 34 | 3 | (400 MHz, DMSO-d$_6$) δ: ppm 5.63 (d, J = 47, 2H), 6.74 (dd, J = 2.7, 1.8, 1H), 8.04 (dd, J = 1.5, 0.6, 1H), 8.13 (d, J = 1.5, 1H), 8.57 (d, J = 1.2, 1H), 8.67 (d, J = 1.5, 1H), 8.79 (td, J = 2.7, 1.1, 2H), 9.21 (d, J = 1.2, 1H) | m/z 280.1 (M + H)$^+$ (ES$^+$), at 3.77 min, 100% |
| 17 | 3-chloro-5-[6-(5-fluoropyridin-2-yl)pyrimidin-4-yl]benzonitrile | 18, 30 | 4 or 5 | (400 MHz, DMSO-d$_6$) δ: ppm 8.02 (td, J = 8.7, 2.7, 1H) 8.29 (dd, J = 2.0, 1.4, 1H) 8.57-8.67 (m, 2H) 8.76 (t, J = 1.5, 1H) 8.84 (d, J = 2.7, 1H) 8.95 (d, J = 1.5, 1H) 9.44 (d, J = 1.2, 1H) | m/z not observed (ES$^+$), at 4.72 min, 100% |
| 18 | 5-[6-(5-fluoropyridin-2-yl)pyrimidin-4-yl]benzene-1,3-dicarbonitrile | 24, 30 | 4 | (400 MHz, DMSO-d$_6$) δ: ppm 8.03 (td, J = 8.7, 2.7, 1H) 8.60 (dd, J = 8.9, 4.6, 1H) 8.69 (t, J = 1.4, 1H) 8.85 (d, J = 2.7, 1H) 9.01-9.14 (m, 3H) 9.47 (d, J = 1.2, 1H) | m/z not observed (ES$^+$), at 3.95 min, 100% |
| 19 | 3-chloro-5-[6-(5-methylpyridin-2-yl)pyrimidin-4-yl]benzonitrile | 18, 31 | 4 | (400 MHz, DMSO-d$_6$) δ: ppm 2.44 (s, 3H) 7.87-7.92 (m, 1H) 8.27-8.30 (m, 1H) 8.42 (d, J = 7.9, 1H) 8.63-8.69 (m, 2H) 8.75 (t, J = 1.4, 1H) 8.96 (d, J = 1.2, 1H) 9.41 (d, J = 1.2, 1H) | m/z not observed (ES$^+$), at 4.77 min, 100% |
| 20 | 3-chloro-5-[6-(5-chloropyridin-2-yl)pyrimidin-4-yl]benzonitrile | 18, 32 | 4 | (400 MHz, DMSO-d$_6$) δ: 8.23 (dd, J = 8.5, 2.7, 1H) 8.28-8.32 (m, 1H) 8.52 (d, J = 8.5, 1H) 8.65 (t, J = 1.7, 1H) 8.76 (t, J = 1.5, 1H) 8.88 (d, J = 2.1, 1H) 8.97 (d, J = 1.2, 1H) 9.45 (d, J = 1.2, 1H) | m/z not observed (ES$^+$), at 5.21 min, 100% |
| 21 | 5-[6-(pyridin-2-yl)pyrimidin-4-yl]benzene-1,3-dicarbonitrile | 3, 24 | 4 | (400 MHz, DMSO-d$_6$) δ: ppm 7.67 (ddd, J = 7.6, 4.8, 1.1, 1H) 8.10 (td, J = 7.7, 1.7, 1H) 8.53 (d, J = 7.9, 1H) 8.69 (t, J = 1.4, 1H) 8.85 (d, J = 4.0, 1H) 9.08 (d, J = 1.5, 3H) 9.47 (d, J = 1.2, 1H) | m/z not observed (ES$^+$), at 3.57 min, 98% |
| 22 | 3-chloro-4-fluoro-5-[6-(5-fluoropyridin-2-yl)pyrimidin-4-yl]benzonitrile | 16, 30 | 4 | (400 MHz, DMSO-d$_6$) δ: ppm 8.03 (td, J = 8.7, 3.1, 1H) 8.51-8.56 (m, 2H) 8.62 (dd, J = 8.9, 4.6, 1H) 8.80 (s, 1H) 8.84 (d, J = 3.1, 1H) 9.50 (d, J = 1.2, 1H) | m/z not observed (ES$^+$), at 4.72 min, 98% |
| 23 | 3-methyl-5-[6-(5-methylpyridin-2-yl)pyrimidin-4-yl]benzonitrile | 21, 33 | 4 | (400 MHz, CDCl$_3$) δ: ppm 2.49 (s, 3H), 2.55 (s, 3H), 7.63 (d, J = 0.6, 1H), 7.74 (dd, J = 8.1, 1.7, 1H), 8.30 (d, J = 0.6, 1H), 8.37 (s, 1H), 8.47 (d, J = 7.9, 1H), 8.62 (d, J = 2.1, 1H), 8.81 (d, J = 1.2, 1H), 9.35 (d, J = 1.5, 1H) | m/z 287.3 (M + H)$^+$ (ES$^+$), at 4.46 min, 100% |
| 24 | 3-[6-(5-fluoropyridin-2-yl)pyrimidin-4-yl]-5-(methoxymethyl)benzonitrile | 30, 39 | 4 | (400 MHz, DMSO-d$_6$) δ: ppm 3.38 (s, 3H), 4.60 (s, 2H), 7.97-8.03 (m, 2H), 8.54-8.60 (m, 2H), 8.66 (t, J = 1.6, 1H), 8.83 (d, J = 2.7, 1H), 8.89 (d, J = 1.2, 1H), 9.41 (d, J = 1.2, 1H) | m/z 321.1 (M + H)$^+$ (ES$^+$), at 3.93 min, 100% |
| 25 | 3-[6-(5-fluoropyridin-2-yl)pyrimidin-4-yl]-5-methoxybenzonitrile | 30, 41 | 4 | (400 MHz, DMSO-d$_6$) δ: ppm 3.94 (s, 3H), 7.67 (dd, J = 2.5, 1.4, 1H), 8.00 (td, J = 8.7, 2.9 Hz, 1H), 8.10 (dd, J = 2.3, 1.6, 1H), 8.31-8.32 (m, 1H), 8.58 (dd, J = 9.0, 4.7, 1H), 8.82 (d, J = 2.7, 1H), 8.88 (d, J = 1.2, 1H), 9.40 (d, J = 1.6, 1H) | m/z 307.2 (M + H)$^+$ (ES$^+$), at 4.08 min, 100% |

Biological Methods

Membrane Preparation cDNA encoding the human mGlu5 receptor was transfected into HEK293 cells using the transfection reagent Genejuice (Novagen). Forty-eight hours after transfection, cells were harvested and washed twice with ice cold phosphate-buffered saline. The pellet was re-suspended in ice-cold buffer containing 20 mM Tris-HCl, pH 7.4, 1 mM EDTA and homogenised with an Ultraturax for 30 s at maximum speed. The suspension was centrifuged (800×g for 5 min at 4° C.) and supernatant collected. Supernatant was centrifuged (40,000×g for 30 min at 4° C.). The resulting pellet was re-suspended and frozen at −80° C. before use. Protein concentration was determined using the BCA protein assay method (Merck Chemicals Ltd).

[$^3$H]-M-MPEP Radioligand Binding Assay

After thawing, membrane homogenates were re-suspended in the binding buffer (50 mM HEPES pH 7.5, 150 mM NaCl) to a final assay concentration of 2.5 µg protein per well. Saturation isotherms were determined by the addition of various concentrations (0-50 nM) of [$^3$H]-M-MPEP (Gasparini et al. *Bioorg. Med. Chem. Lett.* 2002, 12, 407-409) in a total reaction volume of 250 µL for 90 min at rt. At the end of the incubation, membranes were filtered onto a 96-well GF/B filter pre-incubated with 0.1% polyethylenimine, with a Tomtec cell harvester and washed 5 times with 0.5 mL distilled water. Non-specific binding (NSB) was measured in the presence of 0.1 mM MPEP hydrochloride (Tocris bioscience, catalogue number 1212). Radioactivity on the filter was counted (1 min) on a micro-beta counter after addition of 50 µL of scintillation fluid. For competition binding experiments, membranes were incubated with [$^3$H]-M-MPEP at a concentration equal to the K$_D$ value of the radioligand and 10 concentrations of the inhibitory compound (typically between the ranges of 0.1 mM-3.16 pM). IC$_{50}$ values were derived from the inhibition curve and the equilibrium dissociation constant (K$_i$) values were calculated using the Cheng-Prussoff equation. The pK$_i$ values (where pK$_i$=−log$_{10}$ K$_i$) of certain compounds of the invention are tabulated below.

IPone Accumulation Assay

An inducible human mGlu5 receptor HEK293 stable cell line was used with the IPone HTRF assay kit (CisBio). The assay was optimised to measure the ability (potency; pIC$_{50}$)

of antagonists/negative allosteric modulators to reduce agonist (L-quisqualic acid)-induced inositol phosphate turnover. Briefly, cells were plated onto half area 96-well white walled plates at a density of 35,000 cells/well. Sixteen hours post-plating cell growth media was replaced with 25 μL IPone stimulation buffer (supplied in the kit) supplemented with 5 mM sodium pyruvate and 20 μg/mL glutamate pyruvate transaminase. Cells were incubated in a humidified atmosphere for 45 min at 37° C. prior to addition of 5 μL compound for analysis. After a further 15 min incubation time at 37° C., 5 μL of an $EC_{50}$ concentration (30 μM) of L-quisqualic acid (Tocris catalogue number 0188) was added to stimulate inositol phosphate turnover. After 30 min of L-quisqualic acid stimulation the assay was terminated by the addition of detection mixture as per manufacturer's instructions. The concentration of compound which reduced L-quisqualic-stimulated turnover of inositol phosphates by 50% ($IC_{50}$) was calculated. The $pIC_{50}$ values (where $pIC_{50}=-\log_{10} IC_{50}$) of certain compounds of the invention, for instance examples 2, 17 and 18 were $pIC_{50}>8$.

Ex Vivo mGlu5 Receptor Occupancy

Sprague Dawley rats (male; 250-300 g) were dosed orally with either vehicle or examples 2, 17 or 18 (1-10 mg/kg po). Vehicle for example 17 was 10% DMAC+10% solutol HS 15+80% (10% HP-β-CD in water); for example 2 and 18 vehicle was 10% DMAC+5% solutol HS 15+85% (10% VE-TPGS in water). One hour post-dose, animals were sacrificed and whole brains removed, rinsed and blot dried. A coronal block was cut containing the hippocampus and divided along the mid-line and rapidly frozen in isopentane for sectioning and autoradiography. Coronal half-brain sections were cut 20 m thick, approximately 4 mm posterior to the bregma, to incorporate the hippocampal CA3 region. Three adjacent sections were mounted onto slides and incubated with 2 nM [$^3$H]-M-MPEP (total binding) or 2 nM [$^3$H]-M-MPEP and 10 μM fenobam (non-specific binding, Tocris bioscience, catalogue number 2386) for 10 min at room temperature. Binding was terminated by aspiration and washing with ice-cold assay buffer (4×5 min) and sections allowed to air dry. Levels of bound radioactivity in the sections were determined using a beta imager over a 16 h period. Occupancy was determined as mean specific binding with the vehicle treated control taken as 100%. Certain compounds of the invention, for instance example 2, example 17 and 18 occupied hippocampal mGlu5 receptors in a dose-dependent manner, with estimated $ED_{50}$ values of 2.8 mg/kg (po), 0.3 mg/kg (po) and 2.9 mg/kg (po) respectively.

In Vivo Efficacy Test—Marble Burying

Example 17 was assessed for activity in a mouse marble burying test. Male CD-1 mice (25-30 g) were dosed with example 17 (1, 3, 10 and 30 mg/kg, po; n=15/group) or vehicle (10% Solutol HS15+90% (10% $_{(w/v)}$ aqueous HPβCD; n=15/group) 30 min prior to the marble burying test. After 30 min mice were placed individually in a cage containing 24 small glass marbles (diameter ~10 mm) evenly spaced and arranged in a grid-like fashion across the bedding. Thirty minutes later the animals were removed from the cages, and the number of marbles buried by at least two thirds into sawdust were counted and recorded. A one-way ANOVA (analysis of variance) with Dunnett's post-hoc test showed a statistically significant decrease in the number of marbles buried at a dose of 10 and 30 mg/kg versus vehicle group.

| Ex No. | Name | Structure | pKi avg |
|---|---|---|---|
| 1 | 3-chloro-4-fluoro-5-[6-(pyridin-2-yl)pyrimidin-4-yl]benzonitrile | 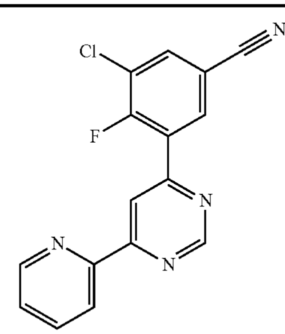 | 8.91 |
| 2 | 3-chloro-5-[6-(pyridin-2-yl)pyrimidin-4-yl]benzonitrile | 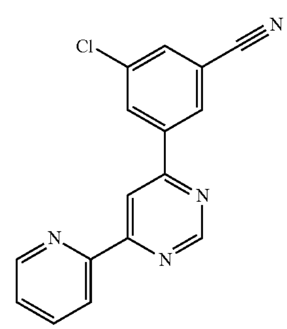 [SMILES: N#Cc1cc(Cl)cc(-c2cc(-c3ccccn3)ncn2)c1] | 8.52 |

-continued
| Ex No. | Name | Structure | pKi avg |
|---|---|---|---|
| 3 | 6-[6-(3-chloro-5-cyanophenyl)pyrimidin-4-yl]pyridine-3-carbonitrile | 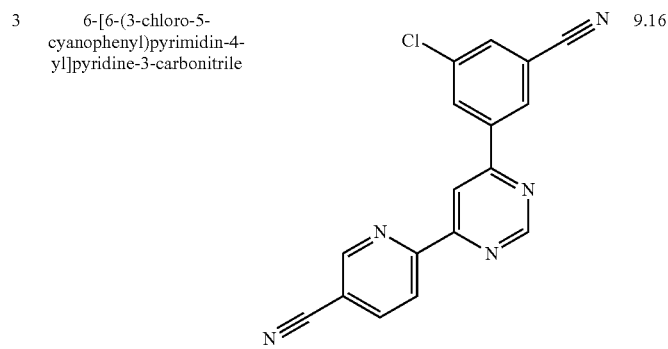 | 9.16 |
| 4 | 3-methyl-5-[6-(pyridin-2-yl)pyrimidin-4-yl]benzonitrile | 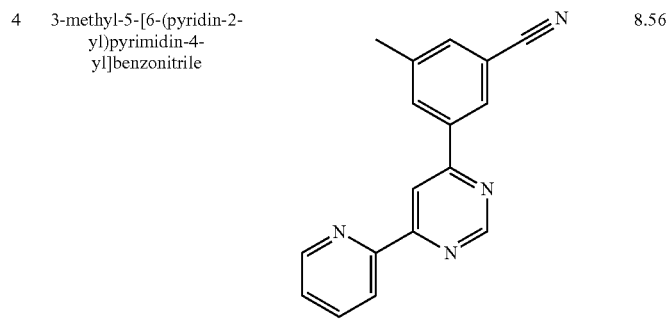 | 8.56 |
| 5 | 3-chloro-5-[6-(pyridazin-3-yl)pyrimidin-4-yl]benzonitrile | 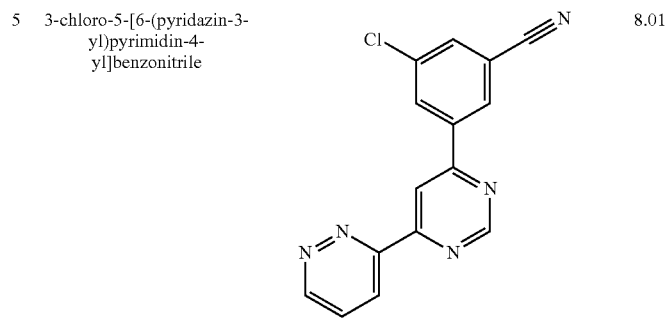 | 8.01 |
| 6 | 3-(4,4'-bipyrimidin-6-yl)-5-chlorobenzonitrile | 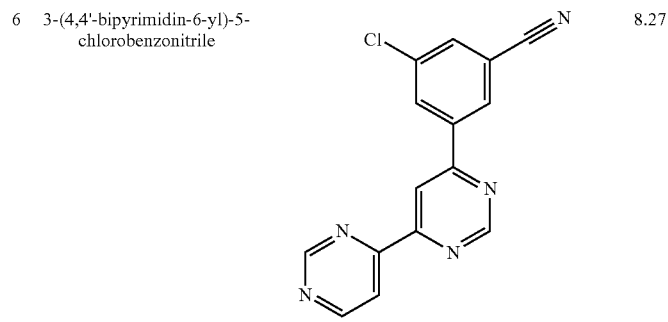 | 8.27 |

-continued

| Ex No. | Name | Structure | pKi avg |
|---|---|---|---|
| 7 | 3-methyl-5-[6-(1H-pyrazol-1-yl)pyrimidin-4-yl]benzonitrile | 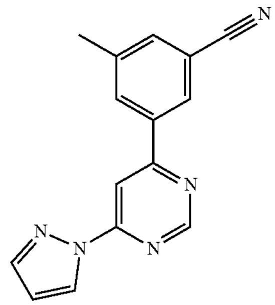 [SMILES: Cc1cc(C#N)cc(-c2cc(-n3cccn3)ncn2)c1] | 8.39 |
| 8 | 3-chloro-5-[6-(1H-pyrazol-1-yl)pyrimidin-4-yl]benzonitrile | 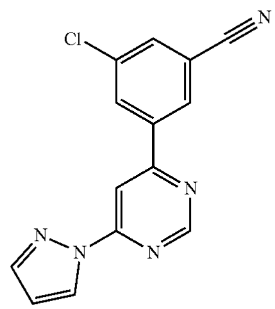 [SMILES: N#Cc1cc(Cl)cc(-c2cc(-n3cccn3)ncn2)c1] | 8.40 |
| 9 | 3-chloro-4-fluoro-5-[6-(1H-pyrazol-1-yl)pyrimidin-4-yl]benzonitrile | 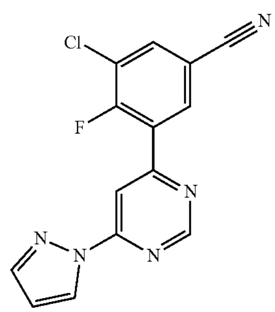 [SMILES: N#Cc1cc(Cl)c(F)c(-c2cc(-n3cccn3)ncn2)c1] | 9.30 |
| 10 | 3-chloro-4-fluoro-5-[4-(1H-pyrazol-1-yl)pyridin-2-yl]benzonitrile | 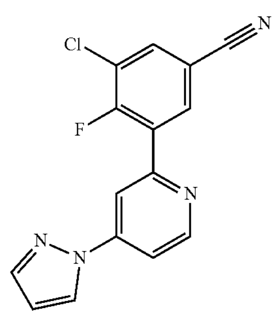 [SMILES: N#Cc1cc(Cl)c(F)c(-c2cc(-n3cccn3)ccn2)c1] | 8.37 |
| 11 | 3-chloro-4-fluoro-5-[2-(1H-pyrazol-1-yl)pyridin-4-yl]benzonitrile | 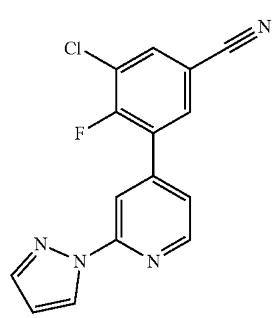 [SMILES: N#Cc1cc(Cl)c(F)c(-c2ccnc(-n3cccn3)c2)c1] | 8.16 |

-continued

| Ex No. | Name | Structure | pKi avg |
|---|---|---|---|
| 12 | 3-chloro-4-fluoro-5-[6-(4-fluoro-1H-pyrazol-1-yl)pyrimidin-4-yl]benzonitrile | 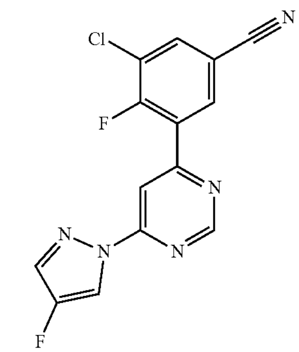 [SMILES: N#Cc1cc(Cl)c(F)c(-c2cc(-n3cc(F)cn3)ncn2)c1] | 8.00 |
| 13 | 3-methyl-5-{6-[($^2$H$_3$)-1H-pyrazol-1-yl]pyrimidin-4-yl}benzonitrile | 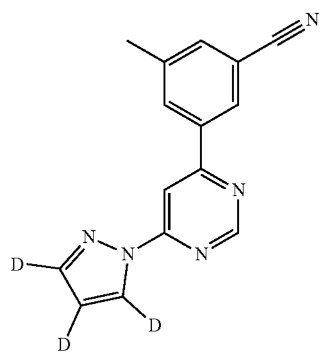 [SMILES: [2H]c1nn(-c2cc(-c3cc(C)cc(C#N)c3)ncn2)c([2H])c1[2H]] | 8.24 |
| 14 | 3-chloro-5-{6-[($^2$H$_3$)-1H-pyrazol-1-yl]pyrimidin-4-yl}benzonitrile | 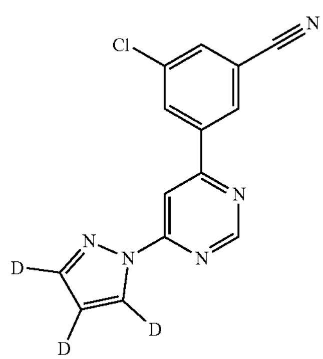 [SMILES: [2H]c1nn(-c2cc(-c3cc(Cl)cc(C#N)c3)ncn2)c([2H])c1[2H]] | 8.56 |
| 15 | 3-chloro-4-fluoro-5-{6-[($^2$H$_3$)-1H-pyrazol-1-yl]pyrimidin-4-yl}benzonitrile | 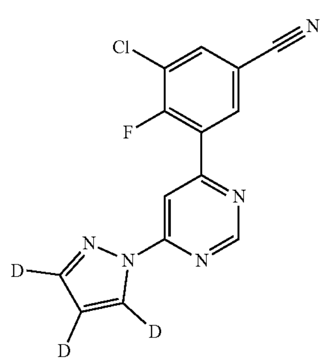 [SMILES: [2H]c1nn(-c2cc(-c3cc(C#N)cc(Cl)c3F)ncn2)c([2H])c1[2H]] | 9.08 |

-continued
| Ex No. | Name | Structure | pKi avg |
|---|---|---|---|
| 16 | 3-(fluoromethyl)-5-[6-(1H-pyrazol-1-yl)pyrimidin-4-yl]benzonitrile | 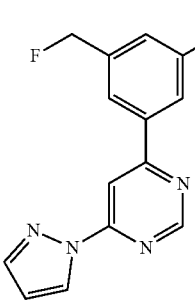 | 8.17 |
| 17 | 3-chloro-5-[6-(5-fluoropyridin-2-yl)pyrimidin-4-yl]benzonitrile | 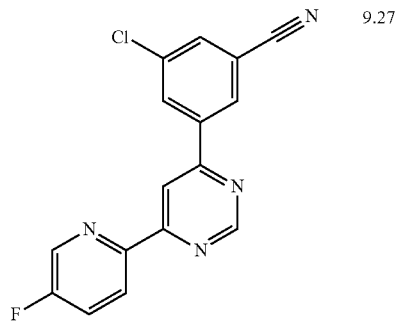 | 9.27 |
| 18 | 5-[6-(5-fluoropyridin-2-yl)pyrimidin-4-yl]benzene-1,3-dicarbonitrile | 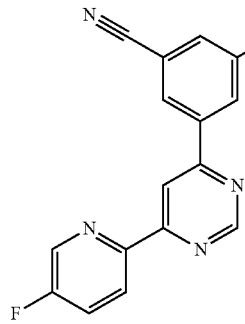 | 8.78 |
| 19 | 3-chloro-5-[6-(5-methylpyridin-2-yl)pyrimidin-4-yl]benzonitrile | 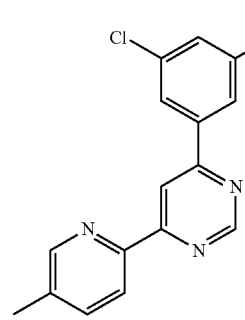 | 8.61 |

-continued
| Ex No. | Name | Structure | pKi avg |
|---|---|---|---|
| 20 | 3-chloro-5-[6-(5-chloropyridin-2-yl)pyrimidin-4-yl]benzonitrile | 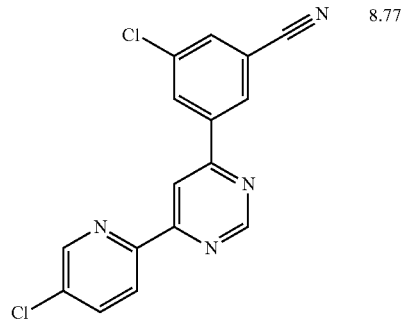 | 8.77 |
| 21 | 5-[6-(pyridin-2-yl)pyrimidin-4-yl]benzene-1,3-dicarbonitrile | 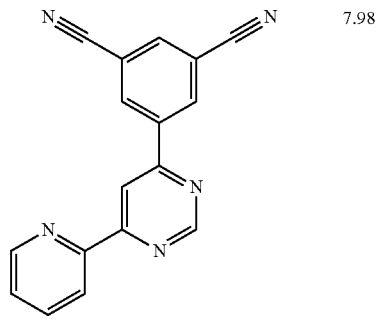 | 7.98 |
| 22 | 3-chloro-4-fluoro-5-[6-(5-fluoropyridin-2-yl)pyrimidin-4-yl]benzonitrile | 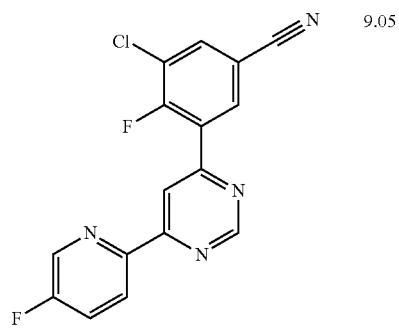 | 9.05 |
| 23 | 3-methyl-5-[6-(5-methylpyridin-2-yl)pyrimidin-4-yl]benzonitrile | 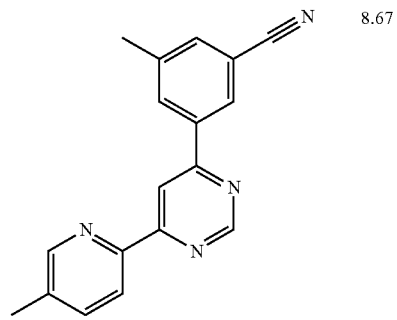 | 8.67 |

| Ex No. | Name | Structure | pKi avg |
|---|---|---|---|
| 24 | 3-[6-(5-fluoropyridin-2-yl)pyrimidin-4-yl]-5-(methoxymethyl)benzonitrile | 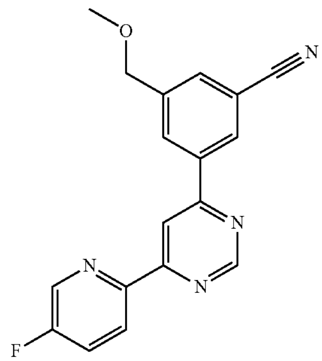 [SMILES: COCc1cc(C#N)cc(-c2cc(-c3ccc(F)cn3)ncn2)c1] | 8.57 |
| 25 | 3-[6-(5-fluoropyridin-2-yl)pyrimidin-4-yl]-5-methoxybenzonitrile | 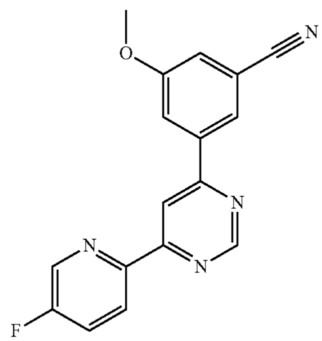 [SMILES: COc1cc(C#N)cc(-c2cc(-c3ccc(F)cn3)ncn2)c1] | 8.37 |

The invention claimed is:

1. A compound of formula (4):

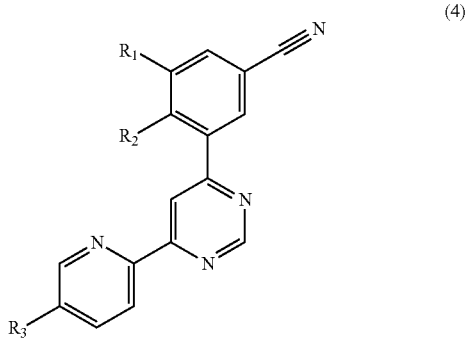

(4)

or a pharmaceutically acceptable salt thereof, wherein
R$_1$ is F, Cl, OMe, CH$_2$OMe, Me, fluoromethyl or cyano;
R$_2$ is H or F;
and
R$_3$ is H, Me, F, Cl or cyano.

2. The compound according to claim 1, wherein R$_1$ is F, Cl or cyano.

3. The compound according to claim 1, wherein R$_3$ is H or F.

4. The compound according to claim 1 which is selected from the group consisting of:
3-chloro-4-fluoro-5-[6-(pyridin-2-yl)pyrimidin-4-yl]benzonitrile,
3-chloro-5-[6-(pyridin-2-yl)pyrimidin-4-yl]benzonitrile,
6-[6-(3-chloro-5-cyanophenyl)pyrimidin-4-yl]pyridine-3-carbonitrile,
3-methyl-5-[6-(pyridin-2-yl)pyrimidin-4-yl]benzonitrile,
3-chloro-5-[6-(5-fluoropyridin-2-yl)pyrimidin-4-yl]benzonitrile,
5-[6-(5-fluoropyridin-2-yl)pyrimidin-4-yl]benzene-1,3-dicarbonitrile,
3-chloro-5-[6-(5-methylpyridin-2-yl)pyrimidin-4-yl]benzonitrile,
3-chloro-5-[6-(5-chloropyridin-2-yl)pyrimidin-4-yl]benzonitrile,
5-[6-(pyridin-2-yl)pyrimidin-4-yl]benzene-1,3-dicarbonitrile,
3-chloro-4-fluoro-5-[6-(5-fluoropyridin-2-yl)pyrimidin-4-yl]benzonitrile,
3-methyl-5-[6-(5-methylpyridin-2-yl)pyrimidin-4-yl]benzonitrile,
3-[6-(5-fluoropyridin-2-yl)pyrimidin-4-yl]-5-(methoxymethyl)benzonitrile,
3-[6-(5-fluoropyridin-2-yl)pyrimidin-4-yl]-5-methoxybenzonitrile,
or a pharmaceutically acceptable salt thereof.

5. The compound according to claim 1 which is 3-chloro-5-[6-(5-fluoropyridin-2-yl)pyrimidin-4-yl]benzonitrile or a pharmaceutically acceptable salt thereof.

6. The compound according to claim 1 which is 5-[6-(5-fluoropyridin-2-yl)pyrimidin-4-yl]benzene-1,3-dicarbonitrile or a pharmaceutically acceptable salt thereof.

7. The compound according to claim 1 which is 3-chloro-5-[6-(5-methylpyridin-2-yl)pyrimidin-4-yl]benzonitrile or a pharmaceutically acceptable salt thereof.

8. The compound according to claim 1 which is 3-chloro-5-[6-(5-chloropyridin-2-yl)pyrimidin-4-yl]benzonitrile or a pharmaceutically acceptable salt thereof.

9. A method for the treatment of migraine, dystonia, depression, anxiety or amyotrophic lateral sclerosis (ALS)

comprising administering an effective amount of a compound according to claim 1 to a subject in need thereof.

10. The method according to claim 9, wherein the disorder is migraine.

11. The method according to claim 9, wherein the disorder is dystonia.

12. The method according to claim 9, wherein the disorder is depression.

13. The method according to claim 9, wherein the disorder is anxiety.

14. The method according to claim 9, wherein the disorder is amyotrophic lateral sclerosis (ALS).

15. The method according to claim 12, wherein the depression is treatment-resistant depression.

* * * * *